(12) United States Patent
Savilahti et al.

(10) Patent No.: US 8,192,934 B2
(45) Date of Patent: Jun. 5, 2012

(54) METHOD FOR DELIVERING NUCLEIC ACID INTO EUKARYOTIC GENOMES

(75) Inventors: Harri Savilahti, Helsinki (FI); Mikko Frilander, Helsinki (FI); Xiaojuan Meng, Helsinki (FI); Anja Paatero, Helsinki (FI); Maria Pajunen, Helsinki (FI); Hikka Turakainen, Espoo (FI)

(73) Assignee: Finnzymes Oy, Espoo (FI)

( * ) Notice: Subject to any disclaimer, the term of this patent is extended or adjusted under 35 U.S.C. 154(b) by 0 days.

(21) Appl. No.: 13/229,258

(22) Filed: Sep. 9, 2011

(65) Prior Publication Data
US 2012/0015831 A1    Jan. 19, 2012

Related U.S. Application Data

(63) Continuation of application No. 10/553,353, filed on May 7, 2007, now Pat. No. 8,026,052.

(30) Foreign Application Priority Data

Apr. 14, 2003  (FI) ..................................... 20030561
Apr. 14, 2004  (WO) .................. PCT/FI2004/000228

(51) Int. Cl.
*C12Q 1/68* (2006.01)
(52) U.S. Cl. .......... 435/6.1; 435/461; 435/462; 435/473
(58) Field of Classification Search ........................ None
See application file for complete search history.

(56) References Cited

OTHER PUBLICATIONS

Lamberg et al., Applied and Environmental Microbiology, Feb. 2002, p. 705-712 vol. 68, No. 2.*
Allet, B. (1979). Mu insertion duplicates a 5 base pair sequence at the host inserted site. Cell 1, vol. 16, 123-129 (Jan. 1979).
Behrens, R., et al. (2000). Fission yeast retrotransposon Tf1 integration is targeted to 5' ends of open reading frames. Nucleic Acids Research 23, 4709-4716.
Butterfield, Y.S., et al. (2002). An efficient strategy for large-scale high-throughput transposon-mediated sequencing of cDNA clones. Nucleic Acids Research 11, 2460-2468.
Chaconas, G., et al. DNA transposition: jumping gene machine, some assembly required. Curr. Biol. 7, 817-82 (1996).
Haapa, S., et al. An efficient DNA sequencing strategy based on the bacteriophage mu in vitro DNA transposition reaction. Genome Res. 3, 308-315 (1999a).
Haapa, S., et al. (1999b). An efficient and accurate integration of mini-Mu transposons in vitro: a general methodology for functional genetic analysis and molecular biology applications. Nucleic Acids Research 13, 2777-2784.
Haapa-Paananen, S., et al. DNA transposition of bacteriophage Mu. A quantitative analysis of target site selection in vitro. J. Biol. Chem. 4, 2843-2851 (2002).
Ji, H., et al. (1993). Hotspots for unselected Ty1 transposition events on yeast chromosome III are near tRNA genes and LTR sequences. Cell 5, 1007-1018.

Kahmann, R., et al. (1979). Nucleotide sequences of the attachment sites of bacteriophage Mu DNA. Nature 5719, 247-250.
Kekarainen, T., et al. (2002). Functional genomics on potato virus a: virus genome-wide map of sites essential for virus propagation. Genome Res. 4, 584-594.
Laurent, L.C., et al. (2000). Functional characterization of the human immunodeficiency virus type 1 genome by genetic footprinting. J. Virol. 6, 2760-2769.
Livingston, D.M., et al. (1979). Isolation of a condensed, intracellular form of the 2-micrometer DNA plasmid of *Saccharomyces cerevisiae*. Proc. Natl. Acad. Sci. U. S. A. 8, 3727-3731.
Miller, S.A., et al. (1988). A simple salting out procedure for extracting DNA from human nucleated cells. Nucleic Acids Research vol. 16, No. 3, 1215.
Mizuuchi, K. (1992). Transpositional recombination: mechanistic insights from studies of mu and other elements. Annu. Rev. Biochem. 1011-1051.
Mizuuchi, M., et al. (1993). Target site selection in transposition of phage Mu. Cold Spring Harb. Symp. Quant. Biol. 515-523.
Nelson, R.G., et al. (1979). Nucleosome organization of the yeast 2-micrometer DNA plasmid: a eukaryotic minichromosome. Proc. Natl. Acad. Sci. U. S. A. 12, 6515-6519.
Raz, E., et al. (1997). Transposition of the nematode *Caenohabditis elegans* Tc3 element in the zebrafish *Danio rerio*. Current Biology 8, 82-88.
Rose, R.E. (1988). The nucleotide sequence of pACYC184. Nucleic Acids Research vol. 16, No. 1, 355.
Rubin, G.M., and Spradling, A.C. (1982). Genetic transformation of *Drosophila* with transposable element vectors. Science 218, 348-353.
Savilahti, H., et al. (1996). Mu transpositional recombination: donor DNA cleavage and strand transfer in trans by the Mu transposase. Cell 2, 271-280.
Savilahti, H., et al. (1995) the phage Mu transpososome core: DNA requirements for assembly and function. EMBO J. 14, 4893-4903.
Taira, S., et al. (1999). Mutational analysis of the *Pseudomonas syringae* pv. tomato hrpA gene encoding Hrp pilus subunit. Mol. Microbiol. 4, 737-744.
Taketo, M., et al. (1980). Association of the 2-micron DNA plasmid with yeast folded chromosomes. Proc. Natl. Acad. Sci. U. S. A. 6, 3144-3148.
Vilen, H., et al. (2001). Construction of gene-targeting vectors: a rapid Mu in vitro DNA transposition-based strategy generating null, potentially hypomorphic, and conditional alleles. Transgenic Res. 1, 69-80.
Vilen, H., et al. (2003). A direct transposon insertion tool for modification and functional analysis of viral genomes. J.Virol. 77, 123-134.
Wach, A., et al. (1994). New heterologous modules for classical or PCR-based gene disruptions in *Saccharomyces cerevisiae*. Yeast 13, 1793-1808.
Winston, F., et al. (1995). Construction of a set of convenient *Saccharomyces cerevisiae* strains that are isogenic to S288C. Yeast 1, 53-55.

* cited by examiner

*Primary Examiner* — Jim Ketter
(74) *Attorney, Agent, or Firm* — Thompson Hine LLP

(57) ABSTRACT

The present invention relates to genetic engineering and especially to the use of DNA transposition complex of bacteriophage Mu. In particular, the invention provides a gene transfer system for eukaryotic cells, wherein in vitro assembled Mu transposition complexes are introduced into a target cell and subsequently transposition into a cellular nucleic acid occurs. The invention further provides a kit for producing insertional mutations into the genomes of eukaryotic cells. The kit can be used, e.g., to generate insertional mutant libraries.

12 Claims, 8 Drawing Sheets

METHOD FOR DELIVERING NUCLEIC ACID INTO EUKARYOTIC GENOMES

This application is a Continuation of allowed co-pending U.S. patent application Ser. No. 10/553,353 filed on May 7, 2007, which claims priority to PCT FI2004/000228 filed Apr. 14, 2004, which claims priority to FI 20040561 filed Apr. 14, 2003, each of which is expressly incorporated by reference herein in its entirety.

The present invention relates to genetic engineering and especially to the use of DNA transposition complex of bacteriophage Mu. In particular, the invention provides a gene transfer system for eukaryotic cells, wherein in vitro assembled Mu transposition complexes are introduced into a target cell. Inside the cell, the complexes readily mediate integration of a transposon construct into a cellular nucleic acid. The invention further provides a kit for producing insertional mutations into the genomes of eukaryotic cells. The kit can be used, e.g., to generate insertional mutant libraries.

BACKGROUND OF THE INVENTION

Efficient transfer of nucleic acid into a target cell is prerequisite for the success of almost any molecular biology application. The transfer of nucleic acid into various types of cells provides means to study gene function in living organisms, to express exogenous genes, or to regulate cell functions such as protein expression. Stably transferred inserts can also be used as primer binding sites in sequencing projects. In principle, the transfer can be classified as transient or stable. In the former case the transferred genetic material will eventually disappear from the target cells. Transient gene transfer typically utilizes plasmid constructions that do not replicate within the host cell. Because vector molecules that would replicate in mammalian cells are scarce, and in essence they are limited to those involving viral replicons (i.e. no plasmids available), the transient transfer strategy is in many cases the only straightforward gene transfer strategy for mammalian cells. For other types of cells, e.g. bacterial and lower eukaryotes such as yeast, replicating plasmids are available and therefore transient expression needs to be used only in certain specific situations in which some benefits can be envisioned (e.g. conditional expression).

In many cases stable gene transfer is the preferred option. For bacteria and lower eukaryotes plasmids that replicate within the cells are available. Accordingly, these DNA molecules can be used as gene delivery vehicles. However, the copy numbers of such plasmids typically exceeds one or two and therefore the transferred genes increase the gene dosage substantially. Typically used plasmids for bacteria and yeasts are present in tens or hundreds of copies. Increased gene dosage compared to normal situation is a potential source of artefactual or at least biased experimental results in many systems. Therefore, it would be advantageous to generate situations in which single-copy gene transfer (per haploid genome) would be possible.

In general, stable single-copy gene transfer can be achieved if transferred DNA can be inserted into the target cell's chromosomal DNA. Traditionally, this has been achieved by using different types of recombination reactions. In bacteria, homologous recombination and site-specific recombination are both widely used and in some cases yet less well characterized "illegitimate" recombination may be used. The choice of a method typically depends on whether a random or targeted mutation is required. While some of these methods are relatively trivial to use for a subset of the bacterial species, a general-purpose method would be more desirable.

Recombination reactions may also be used to stably transfer DNA into eukaryotic cell's chromosomal DNA. Homologous and site-specific recombination reactions produce targeted integrations, and "illegitimate" recombination generates non-targeted events. Utilization of transpositional recombination has been described for baker's yeast *Saccharomyces cerevisiae* (Ji et al 1993) and for fission yeast *Schizosaccharomyces pombe* (Behrens et al 2000). These strategies involve in vivo transposition in which the transposon is launched from within the cell itself. They utilize suitably modified transposons in combination with transposase proteins that are produced within a given cell. Similar systems, in which transposase proteins are produced within cells, are available also for other eukaryotic organisms; typical examples include *Drosophila* and Zebra fish (Rubin and Spradling 1982, Raz et al. 1997).

While transposition systems based on in vivo expression of the transposition machinery are relatively straightforward to use they are not an optimal choice for gene transfer for various reasons. For example, efficiency as well as the host-range may be limited, and target site selection may not be optimal. Viral systems, especially retroviral insertion methods, have been used to generate genomic insertions for animal cells. These strategies also have some disadvantageous properties. For example, immune response may be elicited as a response to virally-encoded proteins, and in general, constructing safe and efficient virus vectors and respective packaging cell lines for a given application is not necessarily a trivial task. Therefore, also for eukaryotic cells, a general-purpose random non-viral DNA insertion strategy would be desirable. Introduction of in vitro-assembled transposition complexes into the cells may be a choice. It is likely that utilization of in vitro-assembled DNA transposition complexes may be one of the most versatile systems for gene transfer. Recently, such a system for bacterial cells has been described and it utilizes chemical reactions based on transpositional DNA recombination (U.S. Pat. Nos. 6,159,736 and 6,294,385). Efficient systems are expected to provide a pool of mutants that can be used various ways to study many types of aspects of cellular life. These mutant pools are essential for studies involving whole genomes (i.e. functional genomics studies). However, a priori it is not possible to envision whether in vitro-assembled DNA transposition complexes would work when introduced into eukaryotic cells, especially if the components are derived from the prokaryota. The difference between prokaryotic and eukaryotic cells, especially the presence of nuclear membrane and packaging of eukaryotic genomic DNA into chromatin structure, may prevent the prokaryotic systems from functioning. In addition, in view of the stability and catalytic activity of the transposition complex, conditions within eukaryotic cells may be substantially different from prokaryotic cells. In addition, other unknown restriction system(s) may fight against incoming DNA and non-specific proteases may destroy assembled transposition complexes before they execute their function for integration. Furthermore, even if the transpositional reaction integrates the transposon into the genome, the ensuing 5-bp single-stranded regions (and in some cases 4-nt flanking DNA flaps) would need to be corrected by the host. Therefore, it is clear that the stability and efficiency of transposition complexes inside a eukaryotic cell cannot be predicted from the results with bacterial cells as disclosed in U.S. Pat. Nos. 6,159,736 and 6,294,385. Thus, to date there is no indication in the prior art that in vitro-assembled transposition complexes can generally be used for nucleic acid transfer into the cells of higher organisms (i.e. eukaryotes).

Bacteriophage Mu replicates its genome using DNA transposition machinery and is one of the best characterized mobile genetic elements (Mizuuchi 1992; Chaconas et al., 1996). We utilised for the present invention a bacteriophage Mu-derived in vitro transposition system that has been introduced recently (Haapa et al. 1999a). Mu transposition complex, the machinery within which the chemical steps of transposition take place, is initially assembled from four MuA transposase protein molecules that first bind to specific binding sites in the transposon ends. The 50 bp Mu right end DNA segment contains two of these binding sites (they are called R1 and R2 and each of them is 22 bp long, Savilahti et al. 1995). When two transposon ends meet, each bound by two MuA monomers, a transposition complex is formed through conformational changes. Then Mu transposition proceeds within the context of said transposition complex, i.e., protein-DNA complexes that are also called DNA transposition complexes or transpososomes (Mizuuchi 1992, Savilahti et al. 1995). Functional core of these complexes are assembled from a tetramer of MuA transposase protein and Mu-transposon-derived DNA-end-segments (i.e. transposon end sequences recognised by MuA) containing MuA binding sites. When the core complexes are formed they can react in divalent metal ion-dependent manner with any target DNA and insert the Mu end segments into the target (Savilahti et al 1995). A hallmark of Mu transposition is the generation of a 5-bp target site duplication (Allet, 1979; Kahmann and Kamp, 1979).

In the simplest case, the MuA transposase protein and a short 50 bp Mu right-end (R-end) fragment are the only macromolecular components required for transposition complex assembly and function (Savilahti et al. 1995, Savilahti and Mizuuchi 1996). Analogously, when two R-end sequences are located as inverted terminal repeats in a longer DNA molecule, transposition complexes form by synapsing the transposon ends. Target DNA in the Mu DNA in vitro transposition reaction can be linear, open circular, or supercoiled (Haapa et al. 1999a).

To date Mu in vitro transposition-based strategies have been utilized efficiently for a variety of molecular biology applications including DNA sequencing (Haapa et al. 1999a; Butterfield et al. 2002), generation of DNA constructs for gene targeting (Vilen et al., 2001), and functional analysis of plasmid and viral (HIV) genomic DNA regions (Haapa et al., 1999b, Laurent et al., 2000). Also, functional genomics studies on whole virus genomes of potato virus A and bacteriophage PRD1 have been conducted using the Mu in vitro transposition-based approaches (Kekarainen et al., 2002, Vilen et al., 2003). In addition, pentapeptide insertion mutagenesis method has been described (Taira et al., 1999). Recently, an insertional mutagenesis strategy for bacterial genomes has been developed in which the in vitro assembled functional transpososomes were delivered into various bacterial cells by electroporation (Lamberg et al., 2002).

*E. coli* is the natural host of bacteriophage Mu. It was first shown with *E. coli* that in vitro preassembled transposition complexes can be electroporated into the bacterial cells whereby they then integrate the transposon construct into the genome (Lamberg et al., 2002). The Mu transpososomes were also able to integrate transposons into the genomes of three other Gram negative bacteria tested, namely, *Salmonella enterica* (previously known as *S. typhimurium*), *Erwinia carotovara*, and *Yersinia enterocolitica* (Lamberg et al. 2002). In each of these four bacterial species the integrated transposons were flanked by a 5-bp target site duplication, a hallmark of Mu transposition, thus confirming that the integrations were generated by DNA transposition chemistry.

SUMMARY OF THE INVENTION

We have developed a gene transfer system for eukaryotic cells that utilizes in vitro-assembled phage Mu DNA transposition complexes. Linear DNA molecules containing appropriate selectable markers and other genes of interest are generated that are flanked by DNA sequence elements needed for the binding of MuA transposase protein. Incubation of such DNA molecules with MuA protein results in the formation of DNA transposition complexes, transpososomes. These can be delivered into eukaryotic cells by electroporation or by other related methods. The method described in the present invention expands the applicability of the Mu transposon as a gene delivery vehicle into eukaryotes.

In a first aspect, the invention provides a method for incorporating nucleic acid segments into cellular nucleic acid of a eukaryotic target cell, the method comprising the step of:

delivering into the eukaryotic target cell a Mu transposition complex that comprises (i) MuA transposases and (ii) a transposon segment that comprises a pair of Mu end sequences recognised and bound by MuA transposase and an insert sequence between said Mu end sequences, under conditions that allow integration of the transposon segment into the cellular nucleic acid.

In another aspect, the invention features a method for forming an insertion mutant library from a pool of eukaryotic target cells, the method comprising the steps of:

a) delivering into the eukaryotic target cell a Mu transposition complex that comprises (i) MuA transposases and (ii) a transposon segment that comprises a pair of Mu end sequences recognised and bound by MuA transposase and an insert sequence with a selectable marker between said Mu end sequences, under conditions that allow integration of the transposon segment into the cellular nucleic acid, b) screening for cells that comprise the selectable marker.

In a third aspect, the invention provides a kit for incorporating nucleic acid segments into cellular nucleic acid of a eukaryotic target cell.

The term "transposon", as used herein, refers to a nucleic acid segment, which is recognised by a transposase or an integrase enzyme and which is essential component of a functional nucleic acid-protein complex capable of transposition (i.e. a transpososome). Minimal nucleic acid-protein complex capable of transposition in the Mu system comprises four MuA transposase protein molecules and a transposon with a pair of Mu end sequences that are able to interact with MuA.

The term "transposase" used herein refers to an enzyme, which is an essential component of a functional nucleic acid-protein complex capable of transposition and which is mediating transposition. The term "transposase" also refers to integrases from retrotransposons or of retroviral origin.

The expression "transposition" used herein refers to a reaction wherein a transposon inserts itself into a target nucleic acid. Essential components in a transposition reaction are a transposon and a transposase or an integrase enzyme or some other components needed to form a functional transposition complex. The gene delivery method and materials of the present invention are established by employing the principles of in vitro Mu transposition (Haapa et al. 1999ab and Savilahti et al. 1995).

The term "transposon end sequence" used herein refers to the conserved nucleotide sequences at the distal ends of a transposon. The transposon end sequences are responsible for identifying the transposon for transposition.

The term "transposon binding sequence" used herein refers to the conserved nucleotide sequences within the transposon end sequence whereto a transposase specifically binds when mediating transposition.

DETAILED DESCRIPTION OF THE INVENTION

Figure 1:
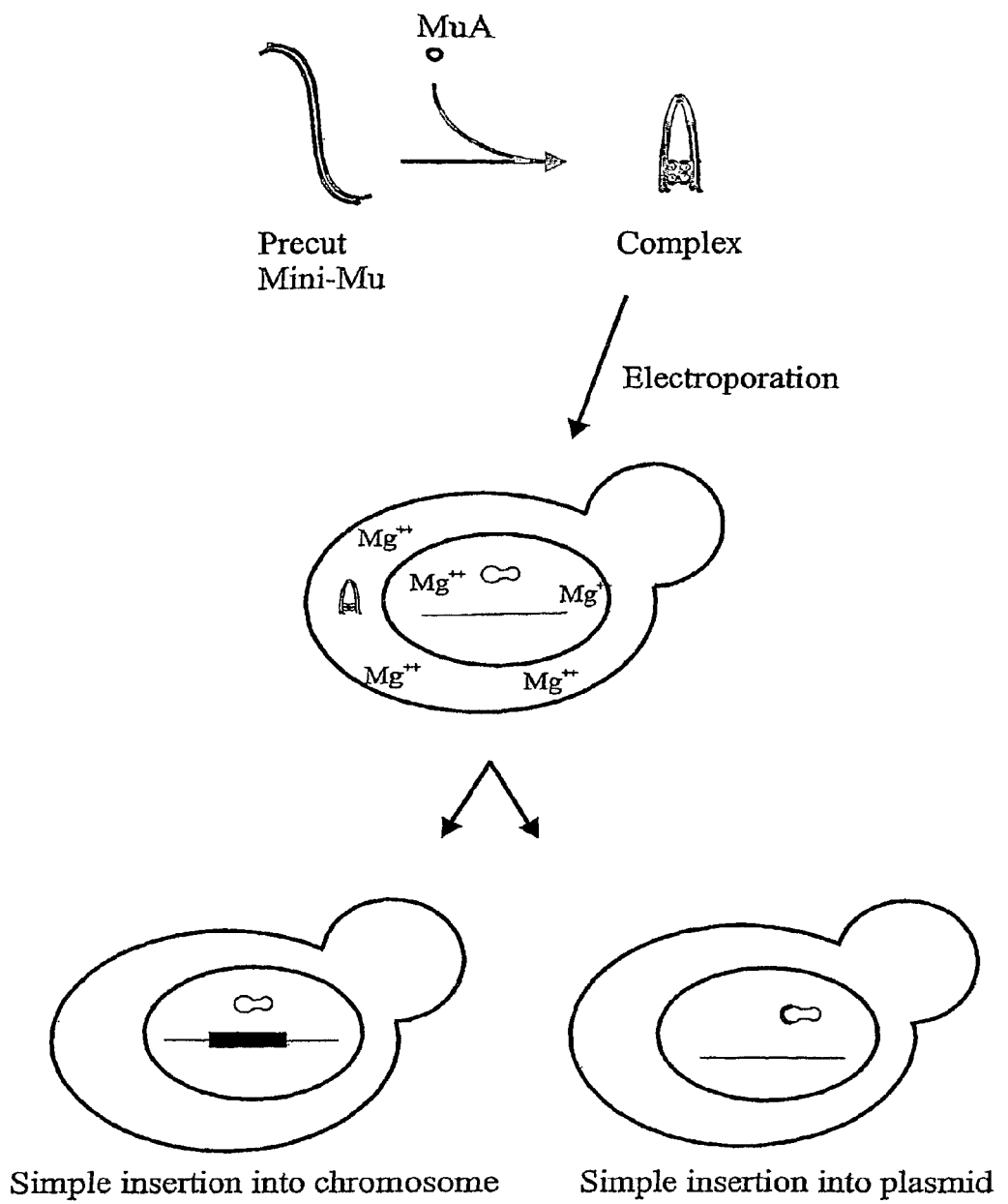
FIG. 1. Mini-Mu transposon integration into the yeast chromosomal or plasmid DNA in vivo by in vitro-assembled Mu transposition complexes comprising of a tetramer of MuA transposase and a mini-Mu transposon.

The in vitro assembled transposition complex is stable but catalytically inactive in conditions devoid of $Mg^{2+}$ or other divalent cations (Savilahti et al., 1995; Savilahti and Mizuuchi, 1996). After electroporation into bacterial cells, these complexes remain functional and become activated for transposition chemistry upon encountering $Mg^{2+}$ ions within the cells, facilitating transposon integration into host chromosomal DNA (Lamberg et al., 2002). The in vitro preassembled transpososomes do not need special host cofactors for the integration step in vivo (Lamberg et al., 2002). Importantly, once introduced into cells and integrated into the genome, the inserted DNA will remain stable in cells that do not express MuA (Lamberg et al., 2002).

To study if the Mu transposition system with the in vitro assembled transpososomes works also for higher organisms we constructed transposons (antibiotic resistance markers connected to Mu ends), assembled the complexes and tested the transposition strategy and target site selection after electroporation of yeast or mouse cells. The transposons were integrated into the genomes with a 5-bp target site duplication flanking the insertion indicating that a genuine DNA transposition reaction had occurred. These results demonstrate that, surprisingly, the conditions in eukaryotic cells allow the integration of Mu DNA. Remarkably, the nuclear membrane, DNA binding proteins, or DNA modifications or conformations did not prevent the integration. Furthermore, the structure and catalytic activity of the Mu complex retained even after repeated concentration steps. This expands the applicability of the Mu transposition strategy into eukaryotes. The benefit of this system is that there is no need to generate an expression system of the transposition machinery for the organism of interest.

The invention provides a method for incorporating nucleic acid segments into cellular nucleic acid of an isolated eukaryotic target cell or a group of such cells (such as a tissue sample or culture), the method comprising the step of:

delivering into the eukaryotic target cell an in vitro assembled Mu transposition complex that comprises (i) MuA transposases and (ii) a transposon segment that comprises a pair of Mu end sequences recognised and bound by MuA transposase and an insert sequence between said Mu end sequences, under conditions that allow integration of the transposon segment into the cellular nucleic acid.

For the method, one can assemble in vitro stable but catalytically inactive Mu transposition complexes in conditions devoid of $Mg^{2+}$ as disclosed in Savilahti et al., 1995 and Savilahti and Mizuuchi, 1996. In principal, any standard physiological buffer not containing $Mg^{2+}$ is suitable for the assembly of said inactive Mu transposition complexes. However, a preferred in vitro transpososome assembly reaction may contain 150 mM Tris-HCl pH 6.0, 50% (v/v) glycerol, 0.025% (w/v) Triton X-100, 150 mM NaCl, 0.1 mM EDTA, 55 nM transposon DNA fragment, and 245 nM MuA. The reaction volume may be for example 20 or 80 microliters. The reaction is incubated at about 30° C. for 0.5-4 h, preferably 2 h. To obtain a sufficient amount of transposition complexes for delivery into the cells, the reaction is then concentrated and desalted from several assembly reactions. For the yeast transformations the final concentration of transposition complexes compared to the assembly reaction is preferably at least tenfold and for the mouse cell transfections at least 20-fold. The concentration step is preferably carried out by using centrifugal filter units. Alternatively, it may be carried out by centrifugation or precipitation (e.g. using PEG or other types of precipitants).

In the method, the concentrated tranposition complex fraction is delivered into the eukaryotic target cell. The preferred delivery method is electroporation. The electroporation of Mu transposition complexes into bacterial cells is disclosed in Lamberg et al., 2002. However, the method of Lamberg et al cannot be directly employed for introduction of the complexes into eukaryotic cells. As shown below in the Experimental Section, the procedure for electroporation of mouse embryonic stem (ES) cells described by Sands and Hasty (1997) can be used in the method of the invention. A variety of other DNA introduction methods are known for eukaryotic cells and the one skilled in the art can readily utilize these methods in order to carry out the method of the invention (see e.g. "Electroporation Protocols for Microorganisms", ed. Jac A. Nickoloff, Methods in Molecular Biology, volume 47, Humana Press, Totowa, N.J., 1995; "Animal Cell Electroporation and Electrofusion Protocols", ed. Jac A. Nickoloff, Methods in Molecular Biology, volume 48, Humana Press, Totowa, N.J., 1995; and "Plant cell Electroporation and Electrofusion Protocols", ed. Jac A. Nickoloff, Methods in Molecular Biology, volume 55, Humana Press, Totowa, N.J., 1995). Such DNA delivery methods include direct injections by the aid of needles or syringes, exploitation of liposomes, and utilization of various types of transfection-promoting additives. Physical methods such as particle bombardment may also be feasible.

Transposition into the cellular nucleic acid of the target cell seems to follow directly after the electroporation without additional intervention. However, to promote transposition and remedy the stress caused by the electroporation, the cells can be incubated at about room temperature to 30° C. for 10 min-48 h or longer in a suitable medium before plating or other subsequent steps. Preferably, a single insertion into the cellular nucleic acid of the target cell is produced.

The eukaryotic target cell of the method may be a human, animal (preferably a mammal), plant, fungi or yeast cell. Preferably, the animal cell is a cell of a vertebrate such as mouse (*Mus musculus*), rat (*Rattus norvegicus*), *Xenopus*, Fugu or zebra fish or an invertebrate such as *Drosophila melanogaster* or *Caenorhabditis elegans*. The plant cell is preferably from *Arabidopsis thaliana*, tobacco or rice. The yeast cell is preferably a cell of *Saccharomyces cerevisiae* or *Schizosaccharomyces pombe*.

The insert sequence between Mu end sequences preferably comprises a selectable marker, gene or promoter trap or enhancer trap constructions, protein expressing or RNA producing sequences. Such constructs renders possible the use of the method in gene tagging, functional genomics or gene therapy.

The term "selectable marker" above refers to a gene that, when carried by a transposon, alters the ability of a cell harboring the transposon to grow or survive in a given growth environment relative to a similar cell lacking the selectable marker. The transposon nucleic acid of the invention preferably contains a positive selectable marker. A positive selectable marker, such as an antibiotic resistance, encodes a product that enables the host to grow and survive in the presence of an agent, which otherwise would inhibit the growth of the organism or kill it. The insert sequence may also contain a reporter gene, which can be any gene encoding a product whose expression is detectable and/or quantitatable by immunological, chemical, biochemical, biological or mechanical assays. A reporter gene product may, for example, have one of the following attributes: fluorescence (e.g., green fluorescent protein), enzymatic activity (e.g., luciferase, lacZ/β-galactosidase), toxicity (e.g., ricin) or an ability to be specifically bound by a second molecule (e.g., biotin). The use of markers and reporter genes in eukaryotic cells is well-known in the art.

Since the target site selection of in vitro Mu system is known to be random or nearly random, one preferred embodiment of the invention is a method, wherein the nucleic acid segment is incorporated to a random or almost random position of the cellular nucleic acid of the target cell. However, targeting of the transposition can be advantageous in some cases and thus another preferred embodiment of the invention is a method, wherein the nucleic acid segment is incorporated to a targeted position of the cellular nucleic acid of the target cell. This could be accomplished by adding to the transposition complex, or to the DNA region between Mu ends in the transposon, a targeting signal on a nucleic acid or protein level. The targeting signal is preferably a nucleic acid, protein or peptide which is known to efficiently bind to or associate with a certain nucleotide sequence, thus facilitating targeting.

One specific embodiment of the invention is the method wherein a modified MuA transposase is used. Such MuA transposase may be modified, e.g., by a deletion, an insertion or a point mutation and it may have different catalytic activities or specifities than an unmodified MuA.

Another embodiment of the invention is a method for forming an insertion mutant library from a pool of eukaryotic target cells, the method comprising the steps of:

a) delivering into the eukaryotic target cell an in vitro assembled Mu transposition complex that comprises (i) MuA transposases and (ii) a transposon segment that comprises a pair of Mu end sequences recognised and bound by MuA transposase and an insert sequence with a selectable marker between said Mu end sequences, under conditions that allow integration of the transposon segment into the cellular nucleic acid.

b) screening for cells that comprise the selectable marker.

In the above method, a person skilled in the art can easily utilise different screening techniques. The screening step can be performed, e.g., by methods involving sequence analysis, nucleic acid hybridisation, primer extension or antibody binding. These methods are well-known in the art (see, for example, Current Protocols in Molecular Biology, eds. Ausubel et al, John Wiley & Sons: 1992). Libraries formed according to the method of the invention can also be screened for genotypic or phenotypic changes after transposition.

Further embodiment of the invention is a kit for incorporating nucleic acid segments into cellular nucleic acid of a eukaryotic target cell. The kit comprises a concentrated fraction of Mu transposition complexes that comprise a transposon segment with a marker, which is selectable in eukaryotic cells. Preferably, said complexes are provided as a substantially pure preparation apart from other proteins, genetic material, and the like.

The publications and other materials used herein to illuminate the background of the invention, and in particular, to provide additional details with respect to its practice, are incorporated herein by reference. The invention will be described in more detail in the following Experimental Section.

EXPERIMENTAL SECTION

Materials and Methods
Strains, Cell Lines and Media

The *Escherichia coli* DH5α was used for bacterial transformations. The bacteria were grown at 37° C. in LB broth or on LB agar plates. For the selection and maintenance of plasmids, antibiotics were used at the following concentrations: ampicillin 100-150 µg/ml, kanamycin 10-25 µg/ml, and chloramphenicol 10 µg/ml. The *Saccharomyces cerevisiae* strain FY1679 (MATa/MATα ura3-52/ura 3-52 his3Δ200/HIS3 leu2Δ1/LEU2 trp1Δ63/TRP1 GAL2/GAL2; Winston et al. 1995) and its haploid derivative FY-3 (MATa HIS LEU TRP ura3-52) were used for yeast transformations. The yeasts were grown on YPD (1% yeast extract, 2% peptone, 2% glucose) or minimal medium (0.67% yeast nitrogen base, 2% glucose). For the selection of the transformants, yeast cells were grown on YPD plates containing 200 μg/ml of G418 (geneticin, Sigma).

The procedures required for propagating mouse AB2.2-Prime embryonic stem (ES) cells (Lexicon Genetics, Inc.) have been described by Sands and Hasty (1997). Briefly, undifferentiated AB2.2-Prime ES cells were grown on 0.1% gelatin (Sigma)-coated tissues culture plates in the ES culture medium consisting of DMEM (Gibco) supplemented with 15% fetal bovine serum (Hyclone), 2 mM L-glutamine (Gibco), 1 mM Sodium pyruvate (Gibco), 100 μM β-Mercaptoethanol and nonessential amino acids (Gibco), 50 U/ml Penicillin, 50 μg/ml Streptomycin (Gibco), and 1000 U/ml LIF (Chemicon).

HeLa S3 cells (ATCC # CCL-2.2) were grown in cell culture medium consisting of MEM supplemented with 10% fetal bovine serum (Gibco Invitrogen), 2 mM L-glutamine (Gibco Invitrogen), 50 U/ml Penicillin (Gibco Invitrogen), and 50 μg/ml Streptomycin (Gibco Invitrogen).

Proteins and Reagents

MuA transposase (MuA), proteinase K, calf intestinal alkaline phosphatase (CIP) and $Cam^R$ Entranceposon (TGS Template Generation System) were obtained from Finnzymes, Espoo, Finland. Restriction endonucleases and the plasmid pUC19 were from New England Biolabs. Klenow enzyme was from Promega. Enzymes were used as recommended by the suppliers. Bovine serum albumin was from Sigma. [$α^{32}P$]dCTP (1000-3000 Ci/mmol) was from Amersham Biosciences.

Construction of kanMX4-Mu Transposons

The kanMX4 selector module (1.4 kb) was released from the pFA6-kanMX4 (Wach et al. 1994) by EcoRI+BglII double digestion and ligated to the 0.75 kb vector containing the pUC miniorigin and the Mu ends, producing the kanMX4-Mu plasmid, pHTH1. Plasmid DNA was isolated with the Plasmid Maxi Kit (QIAGEN). To confirm the absence of mutations in the kanMX4 module the insert was sequenced following the in vitro transposition reaction with the $Cam^R$ Entranceposon as a donor DNA and the plasmid pHTH1 as a target DNA with primers Muc1 and Muc2.

The primers for sequencing the yeast constructs were Muc1: 5'-GCTCTCCCCGTGGAGGTAAT-3' (SEQ ID NO:1) and Muc2: 5'-TTCCGTCACAGGTATTTATTCGGT-3' (SEQ ID NO:2).

We also constructed a transposon with a bacterial replicon between the Mu ends to allow easier outcloning. The p15A replicon was cut from the plasmid pACYC184 (Rose 1988) with SphI, blunted with Klenow enzyme, and ligated into EcoRI-cut end-filled pHTH1 to produce kanMX4-p15A-Mu plasmid, pHTH4.

Construction of Mu/LoxP-Kan/Neo Transposon

A neomycin-resistance cassette containing a bacterial promoter, SV40 origin of replication, SV40 early promoter, kanamycin/neomycin resistance gene, and Herpes simplex virus thymidine kinase polyadenylation signals was generated by PCR from pIRES2-EGFP plasmid (Clontech). After addition of LoxP sites and Mu end sequences using standard PCR-based techniques, the construct was cloned as a BglII fragment into a vector backbone derived from pUC19. The construct (pALH28) was confirmed by DNA sequencing.

Assembly and Concentration of Transpososomes

The transposons (kanMX4-Mu, 1.5 kb; kanMX4-p15A-Mu, 2.3 kb; Mu/LoxP-Kan/Neo, 2.1 kb) were isolated by BglII digestion from their respective carrier plasmids (pHTH1, pHTH4, pALH28). The DNA fragments were purified chromatographically as described (Haapa et al. 1999a).

The standard in vitro transpososome assembly reaction (20 μl or 80 μl) contained 55 nM transposon DNA fragment, 245 nM MuA, 150 mM Tris-HCl pH 6.0, 50% (v/v) glycerol, 0.025% (w/v) Triton X-100, 150 mM NaCl, 0.1 mM EDTA. The reaction was carried out at 30° C. for 2 h. The complexes were concentrated and desalted from several reactions by Centricon concentrator (Amicon) according to manufacturer's instructions and washed once with water. The final concentration for the yeast transformations was approximately tenfold and for the mouse transfections about 20-fold.

Electrocompetent Bacterial and Yeast Cells

Electrocompetent bacterial cells for standard cloning were prepared and used as described (Lamberg et al., 2002). Electrocompetent S. cerevisiae cells were grown as follows. An overnight stationary phase culture was diluted 1:10 000 in fresh YPD (1% yeast extract, 2% peptone, 2% glucose) and grown to $A_{600}$ 0.7-1.2. The cell pellets were collected by centrifugation (5000 rpm), suspended in ¼ volume of 0.1 M lithium acetate, 10 mM dithiothreitol, 10 mM Tris-HCl pH 7.5, 1 mM EDTA (LiAc/DTT/TE) and incubated at room temperature for 1 h. The repelleted cells were washed with ice-cold water and again collected by centrifugation. The pellet was then resuspended in 1/10 of the original volume of ice-cold 1 M sorbitol. Following centrifugation, the pellet was suspended in ice-cold 1 M sorbitol to yield ~200-fold concentration of the original culture density. One hundred microliters of cell suspension were used for each electroporation. For competence status determionation, transpososomes or plasmid DNA were added to the cell suspension and incubated on ice for 5 min. The mixture was transferred to a 0.2 cm cuvette and pulsed at 1.5 kV (diploid FY 1679) or 2.0 kV (haploid FY-3), 25 μF, 200 ohms with Bio-Rad Genepulser II. After electroporation 1 ml of YPD was added, and cultures were incubated at 30° C. for 0-4 hours. Subsequently cells were plated on YPD plates containing 200 μg/mlof G418. The competent status of the yeast strains was evaluated in parallel by electroporation of a control plasmid pYC2/CT (URA3, CEN6/ARSH4, $amp^R$, pUC ori, Invitrogen) and plating the cells on minimal plates.

Mouse ES Cell Transfection and Colony Isolation

The procedures used for electroporation of mouse AB2.2-Prime embryonic stem (ES) cells have been described by Sands and Hasty (1997). Briefly, the AB2.2-Prime ES cells were collected in phosphate-buffered saline (PBS) at a density of $11×10^6$ cells/ml. 2.2-2.3 μg of the transposon complexes or linearized DNA was added to an 0.4 cm electroporation cuvette. For each electroporation, 0.9 ml of ES cell suspension (approximately $10×10^6$ cells) was mixed with transpososomes or linear DNA. Electroporation was carried out using Bio-Rad's Gene Pulser and Capacitance Extender at 250 V, 500 μF. After electroporation the cells stood at RT for 10 min and were then plated in gelatin coated plates. The electroporated ES cells were cultured in the conditions mentioned above for 24-48 hours before adding G418 (Gibco) to a final concentration of 150 μg/ml to select transposon insertions. Transfected colonies of ES cells were picked after 10 days in selection and individual colonies were cultured in separate wells of the 96-wells or 24-wells plates using the conditions described above.

HeLa Cell Transfection and Colony Isolation

The HeLa cells were electroporated basically according to the instructions by ATCC. Briefly, the HeLa cells were collected in phosphate-buffered saline (PBS) at a density of $1.8×10^6$ cells/ml. 2-2.3 μg of the transposon complexes or linearized transposon DNA was added to an 0.4 cm electroporation cuvette. For each electroporation, 0.9 ml of HeLa cell suspension (approximately $1.6×10^6$ cells) was mixed with transpososomes or linear DNA. Electroporation was carried out using Bio-Rad's Gene Pulser and Capacitance extender at 250 V, 500 µF. After electroporation the cells stood at RT for 10 min and were then plated. The electroporated cells were then cultured in the conditions mentioned above for 60 hours before adding G418 (Gibco Invitrogen) to a final concentration of 400 µg/ml to select transposon insertions. Transfected colonies of HeLa cells were picked after 10-11 days in selection and individual colonies were cultured first in separate wells of the 96-wells plate, and transferred later to separate wells of 24-wells or 6-wells plates and 10 cm plates using the conditions described above.

Isolation of Genomic DNA

Yeast Genomic DNA of each geneticin resistant yeast clone was isolated either with QIAGEN Genomic DNA Isolation kit or according to Sherman et al., 1981.

Mouse ES cells Genomic DNA was isolated from ES cell essentially according to the method developed by Miller et al. (1988). ES cells were collected from individual wells from the 24-well cultures and suspended to 500 µl of the proteinase K digestion buffer (10 mM Tris-HCl (pH 8.0), 400 mM NaCl, 10 mM EDTA, 0.5% SDS, and 200 µg/ml proteinase K). The proteinase K treatment was carried out for 8-16 hours at 55° C. Following the proteinase K treatment 150 µl of 6 M NaCl was added followed by centrifugation at microcentrifuge (30 min, 13 K). The supernatant was collected and precipitated with ethanol to yield DNA pellet that was washed with 70% ethanol and air-dried. DNA was dissolved in TE (10 mM Tris-HCl, pH 8.0 and 1 mM EDTA) buffer.

HeLa cells Genomic DNA was isolated from HeLa cells essentially according to the method developed by Miller et al. (1988). HeLa cells were collected from three 10 cm plates and suspended to 15 ml of proteinase K digestion buffer (10 mM Tris-HCl (pH 8.0), 400 mM NaCl, 10 mM EDTA, 0.5% SDS, and 200-400 µg/ml proteinase K). The proteinase K treatment was carried out at 55° C. for 16-48 hours or until no cells were visible. RNase was added at 25-50 µg/ml and incubated at 37° C. for 8-24 hours. Following the RNase treatment 4.5 ml of 6 M NaCl was added followed by centrifugation (SS-34, 11.6-14 K, 20-30 min, 4° C.). The supernatant was collected and precipitated with ethanol to yield DNA pellet that was washed with 70% ethanol and air-dried. DNA was dissolved in TE (10 mM Tris-HCl (pH 8.0) and 1 mM EDTA) buffer.

Southern Blot

Yeast The DNA was digested with appropriate enzymes. The fragments were electrophoresed on a 0.8% agarose gel and blotted onto Hybond N+ membrane (Amersham). Southern hybridisation was carried out with [$\alpha^{32}$P]dCTP-labelled (Random Primed, Roche) kanMX4 (BglII-EcoRI fragment) as a probe.

Mouse ES cells DNA Southern blot hybridisation was performed according to standard methods as described (Sambrook, et al., 1989). 10-15 µg of the wild type and transfected AB2.2-Prime ES cell DNAs were digested with various restriction enzymes and separated on 0.8% agarose gels. The DNA was transferred to a nylon filter (Hybond N+, Amersham) and fixed with UV (Stratalinker, Statagene). Inserted DNA was visualized by hybridisation with a [$\alpha$-$^{32}$p]dCTP-labeled (Rediprimell, Amersham) DNA probes (Mu/LoxP-Kan/Neo BamHI fragment). Hybridisation was performed at 65° C. for 16 hours in solutions containing 1.5×SSPE, 10% PEG 6000, 7% SDS, 100 µg/ml denatured herring sperm DNA. After the hybridisation, the filter was washed twice 5 min and once 15 min in 2×SSC, 0.5% SDS at 65° C. and once or twice for 10-15 min in the 0.1×SSC, 0.1% SDS at 65° C. The filter was exposed to a Fuji phosphoimager screen for 8-16 hours and processed in a FujiBAS phosphoimager.

HeLa cells Southern blot hybridisation was performed according to standard methods as described (Sambrook et al., 1989). 10 µg of the wild type and transfected HeLa cell DNAs were digested with NheI+SpeI and separated on 0.8% agarose gel. The DNA was transferred to a nylon filter (Hybond N+, Amersham) and fixed with UV (Stratalinker, Stratagene). Inserted transposon DNA was visualized by hybridisation with a [$\alpha$-$^{32}$P]dCTP-labeled (Rediprimell, Amersham) DNA probe (Mu/LoxP-Kan/Neo transposon). Hybridisation was performed at 65° C. for 16 hours in solutions containing 1.5×SSPE, 10% PEG 6000, 7% SDS, 100 µg/ml denatured herring sperm DNA. After the hybridisation, the filter was washed three times for 20-40 min in 2×SSC, 0.5% SDS at 65° C. and three times for 20-40 min in 0.1×SSc, 0.1% SDS at 65° C. The filter was exposed to a Fuji phosphoimager screen for 8-16 hours and processed in a FujiBAS phosphoimager Determination of Target Site Duplication Cloning. Yeast genomic DNA was digested with BamHI+BglII, SalI+XhoI or PvuII to produce a fragment with a transposon attached to its chromosomal DNA flanks. These fragments were then cloned into pUC19 cleaved with BamHI, SalI or SmaI, respectively, selecting for kanamycin and ampicillin resistance. Alternatively, clones transfected with kanMX4-p15A were cleaved with BamHI+BglII, ligated, electroporated and selected for resistance produced by the transposon containing fragments. DNA sequences of transposon borders were determined from these plasmids using transposon specific primers SeqA and Seq MX. Genomic locations were identified using the BLAST search at SGD (Saccharomyces Genome Database; http://genome-www-.stanford.edu/Saccharomyces/) or SDSC Biology WorkBench (http://workbench.sdsc.edu/) servers.

The primers for sequencing the ends of cloned yeast inserts were Seq A: 5'-ATCAGCGGCCGCGATCC-3' (SEQ ID NO:3) and Seq MX4: 5'-GGACGAGGCAAGCTAAACAG-3' (SEQ ID NO:4).

PCR amplification. Two micrograms of yeast genomic DNA was digested with BamHI+BglII or NheI+SpeI. Specific partially double-stranded adapters were made by annealing 2 µM adapter primer 1 (WAP-1) with complementary 2 µM adapter primer 2 (WAP-2*), 3 (WAP-3*), or 4 (WAP-4*). The 3' OH group of the WAP-2*, WAP-3*, and WAP-4* primers was blocked by a primary amine group and the 5' ends were phosphorylated. The restriction fragments (200 ng) generated by BamHI+BglII were ligated with 22 ng of adapter that was made by annealing primers WAP-1 and WAP-2*, whereas the restriction fragments generated with NheI+SpeI were ligated with the 22 ng of adapter made by annealing primers WAP-1 and WAP-3*. One fifth of the ligation reaction was used as a template to perform PCR amplification at 20 µl to enrich for DNA fragments between the adapter and the transposon with primers Walker-1 and TEFterm-1 or Walker-1 and TEFprom-1. PCR conditions were 94° C., 1 min, 55° C., 1 min, 72° C., 4 min for 30 cycles. Nested PCR was carried out at 50 µl using 2 □l of one hundred-fold diluted primary PCR products as a template using primers Walker-2 and TEFterm-2 or Walker-2 and TEFprom-2 for PCR products produced from BamHI+BglII fragments and Walker-3 and TEFterm-2 or Walker-3 and TEFprom-2 for PCR products produced from the NheI+SpeI fragments. The PCR conditions were as before. The amplified nested PCR products were sequenced using sequencing primer Mu-2.

One microgram of mouse genomic DNA was digested with BglII+BclI or NheI+SpeI. Specific partially double-stranded adapters were made as for the yeast. The restriction fragments (400 ng) generated by BclI+BglII were ligated with 44 ng of adapter that was made by annealing primers WAP-1 and WAP-2*, whereas the restriction fragments (200 ng) generated with NheI+SpeI were ligated with the 22 ng of adapter made by annealing primers WAP-1 and WAP-3*. Respectively, one fourth or one fifth of the ligation reaction was used as a template to perform PCR amplification at 20 µl to enrich for DNA fragments between the adapter and the transposon with primers Walker-1 and HSP430 or Walker-1 and HSP431. PCR conditions were 94° C., 1 min, 55° C., 1 min, 72° C., 4 min for 30 cycles. Nested PCR was carried out at 50 µl using 2 µl of eighty fold or one hundred-fold diluted primary PCR products as a template using primers Walker-2 and HSP429 or Walker-2 and HSP432 for PCR products produced from BcII+BglII fragments and Walker-3 and HSP429 or Walker-3 and HSP432 for PCR products produced from the NheI+SpeI fragments. The PCR conditions were as before. The amplified nested PCR products were sequenced using sequencing primer Mu-2.

```
Primers for PCR-based detection:
                                     (SEQ ID NO: 5)
WAP-1            CTAATACCACTCACATAGGGCGGCCGCCCGGGC (SEQ ID NO: 6)
WAP-2*           GATCGCCCGGGCG-NH2

(SEQ ID NO: 7)
WAP-3*           CTAGGCCCGGGCG-NH2

(SEQ ID NO: 8)
WAP-4*           AATTGCCCGGGCG-NH2

(SEQ ID NO: 9)
Walker-1         CTAATACCACTCACATAGG (SEQ ID NO: 10)
Walker-2         GGGCGGCCGCCCGGGCGATC (SEQ ID NO: 11)
Walker-3         GGGCGGCCGCCCGGGCCTAG (SEQ ID NO: 12)
Walker-4         GGGCGGCCGCCCGGGCAATT (SEQ ID NO: 13)
TEFterm-1        CTGTCGATTCGATACTAACG (SEQ ID NO: 14)
TEFterm-2        CTCTAGATGATCAGCGGCCGCGATCCG (SEQ ID NO: 15)
TEFprom-1        TGTCAAGGAGGGTATTCTGG (SEQ ID NO: 16)
TEFprom-2        GGTGACCCGGCGGGACGAGGC (SEQ ID NO: 17)
Mu-2             GATCCGTTTTCGCATTTATCGTG (SEQ ID NO: 18)
HSP429           GGCCGCATCGATAAGCTTGGGCTGCAGG (SEQ ID NO: 19)
HSP430           ACATTGGGTGGAAACATTCC (SEQ ID NO: 20)
HSP431           CCAAGTTCGGGTGAAGGC (SEQ ID NO: 21)
HSP432           CCCCGGGCGAGTCTAGGCCGC
```

HeLa cells The genomic HeLa cell DNA was digested with BamHI+BcII to produce a fragment with a transposon attached to its chromosomal DNA flanks. These fragments were then cloned into pUC19 cleaved with BamHI, selecting for kanamycin and ampicillin resistance. DNA sequences of transposon borders were determined from these plasmids using transposon specific primers HSP430 and HSP431. Genomic locations were identified using the SSAHA search at Ensembl Human Genome Browser Release 20.34c.1 which is based on the NCBI 34 assembly of the human genome.

Results

Transposon Construction and its Introduction to the Cells

Figure 2A:
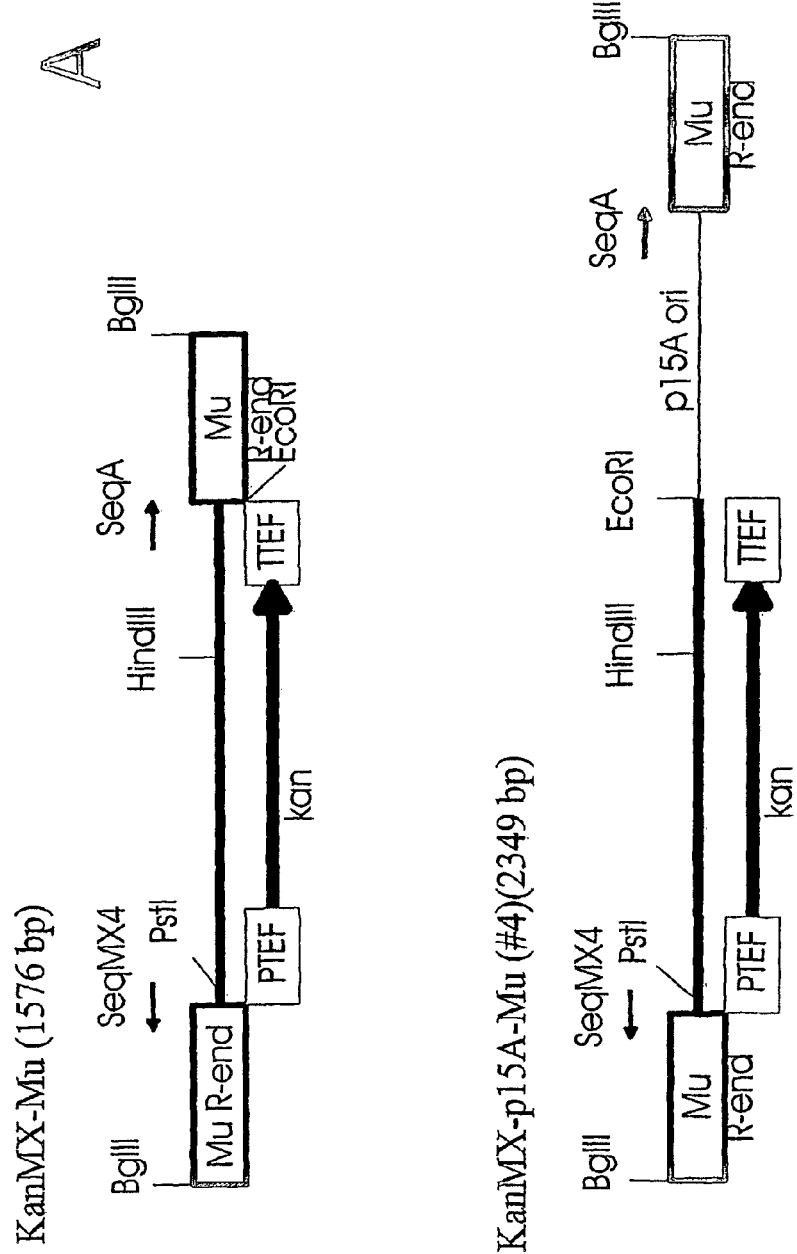
FIGS. 2A and 2B. Schematic representation of the Mu-transposons used in this study with the relevant restriction sites. (2A) Both of the yeast transposons contain TEF promoter ($P_{TEF}$), kan marker gene and TEF terminator ($T_{TEF}$) embedded between two 50 bp Mu right end sequences. The kanMX4-p15A-Mu transposon contains the additional p15A replicon. Short arrows denote the binding sites of the primers used for sequencing of the out-cloned flanking sequences. The BglII sites in the ends are used to excise the transposon from the vector plasmid backbone. (2B) The Mu/LoxP-Kan/Neo transposon for transfecting the mouse ES cells. It contains kan/neo marker gene between two Mu right end and LoxP sequences. The kan/neo marker includes the prokaryotic and eukaryotic promoters and terminators as explained in Materials and methods.
Figure 2B:
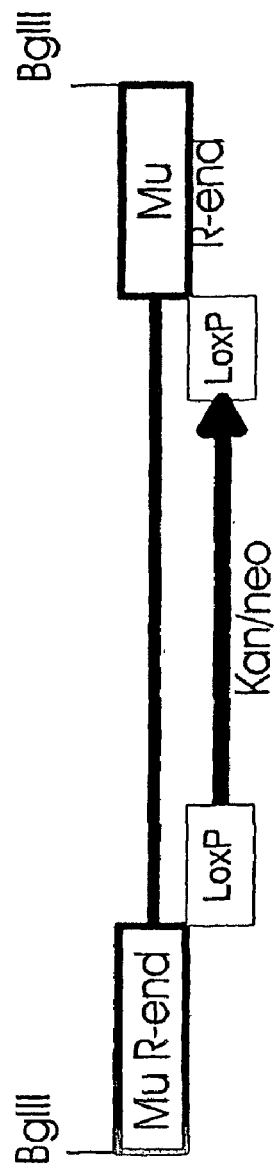
Figure 3:
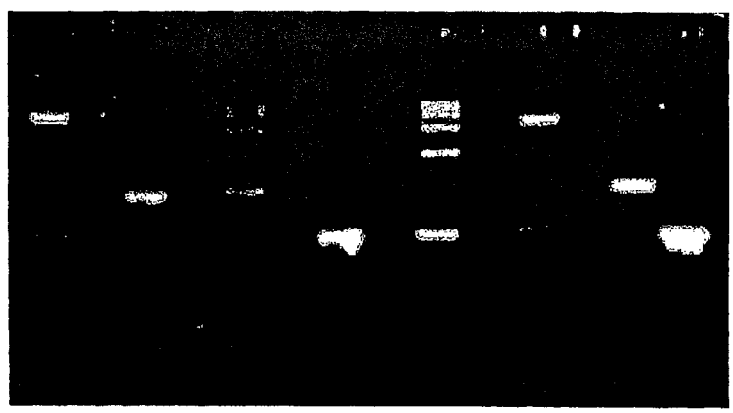
FIG. 3. Mu transposition complex formation with KanMX4-Mu (1.5 kb) and KanMX4-p15A-Mu (2.3 kb) substrates analysed by agarose gel electrophoresis. Substrate DNA was incubated with or without MuA, and the reaction products were analysed in the presence or absence of SDS. Samples were electrophoresed on 2% agarose gel containing 87 mg/ml of heparin and 87 mg/ml of BSA.

To study if the Mu transposition system works also for eukaryotes (FIG. 1) we constructed a kanMX4-Mu transposon containing the $kan^R$ gene from Tn903 and translational control sequences of the TEF gene of Ashbya gossypii between the Mu ends, with or without additional bacterial p15A replicon between the Mu ends (FIG. 2A). We studied the assembly of Mu transpososomes by incubating MuA protein with the kanMX4-Mu transposon and detected stable protein-DNA complexes by agarose gel electrophoresis (FIG. 3). The reactions with kanMX4-Mu and kanMX-p15A-Mu transposons produced several bands of protein-DNA complexes that disappeared when the sample was loaded in the presence of SDS indicating that only non-covalent protein-DNA interactions were involved in the complexes. An aliquot of assembly reactions with and without MuA transposase were electroporated into Saccharomyces cerevisiae cells and the yeasts were scored for geneticin resistance. The competent status of the yeast strains was evaluated in parallel by electroporation of a control plasmid pYC2/CT. The electroporation efficiency with the transpososomes into the yeast was approximately three orders of magnitude lower than the efficiency with the plasmid (Table 1). This result is consistent with previous results with bacteria (Lamberg et al 2002). Only the sample containing detectable protein-DNA complexes yielded geneticin resistant colonies.

For mouse experiments we constructed a Mu/loxP-Kan/Neo transposon that contained bacterial and eukaryotic promoters, kanamycin/neomycin resistance gene, and Herpes simplex virus thymidine kinase polyadenylation signals (FIG. 26). The transfection of the mouse ES cells with the transpososome resulted in 1720 G418 resistant colonies per µg DNA and the linear control in 330 resistant colonies per µg DNA. Thus the transfection with the transpososome yielded over 5 times more resistant colonies per µg DNA. The control cells with no added DNA did not produce any resistant colonies.

In HeLa cells, transfection with the transpososomes resulted in about $10^3$ resistant colonies per µg DNA and transfection with the linear control DNA resulted in about $10^1$ resistant colonies per µg DNA. Thus the transpososomes were significantly more efficient in generating transfectants. The control cells with no added transposon did not produce any resistant colonies.

Integration of the Transposon into the Genome

Figures 4A, 4B:
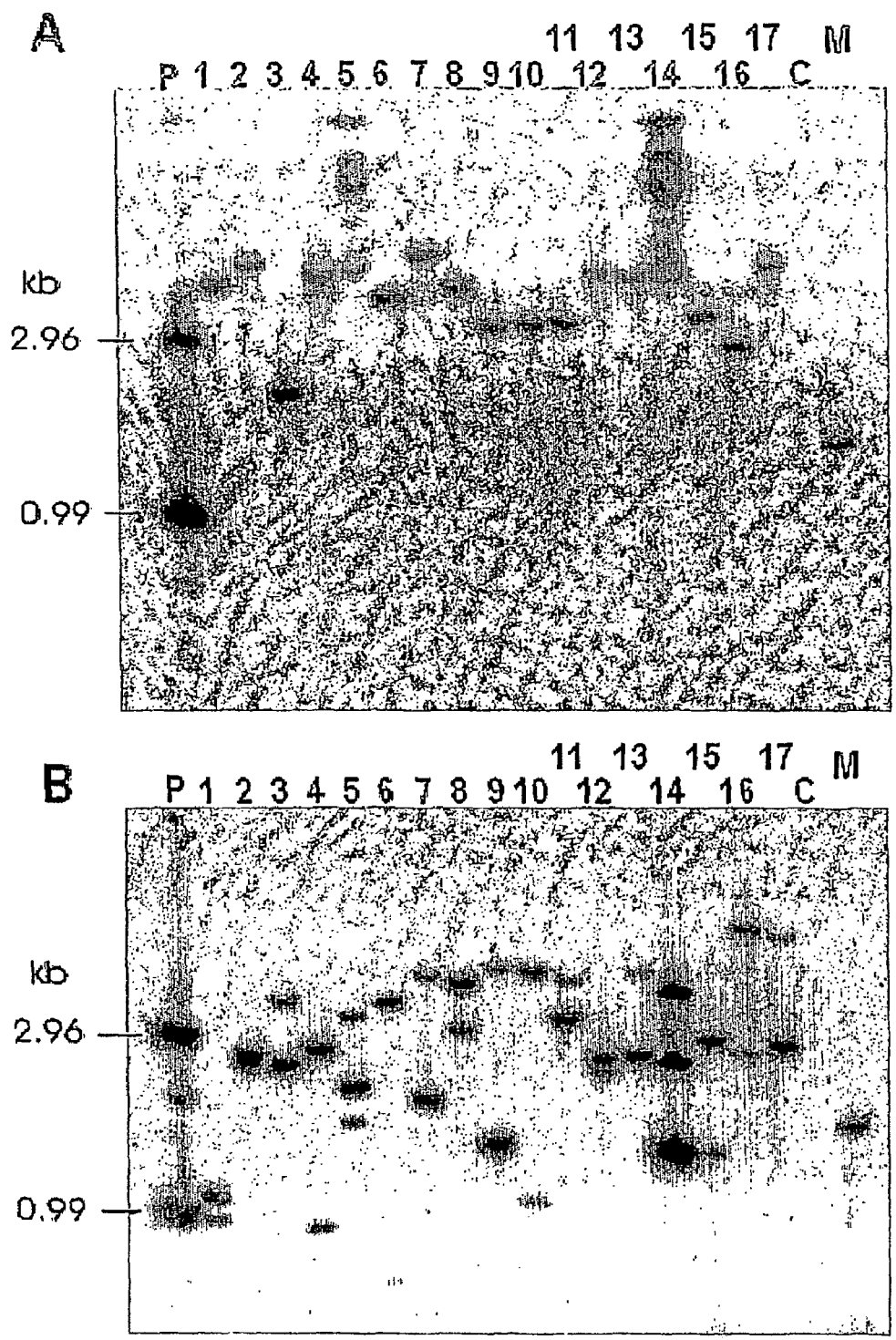
FIGS. 4A and 4B. Southern blot analysis of the insertions into the yeast genome. Genomic DNA of 17 geneticin-resistant FY1679 clones, resulting from the electroporation of the transposition complexes into yeast cells, was digested with BamHI+BglII (4A) or HindIII (4B) and probed with kanMX4 DNA. Lanes 1-17, transposon insertion mutants; C, genomic DNA of original *S. cerevisiae* FY1679 recipient strain as a negative control; P, linearized plasmid DNA containing kanMX4-Mu transposon as a positive control; M, molecular size marker. The sizes of plasmid fragments are shown on the left.

Southern blot analysis can be used to study whether the transposon DNA was inserted into the genomic DNA of the geneticin-resistant colonies. Digestion of genomic DNA with enzyme(s) which do not cut the transposon produces one fragment hybridising to the transposon probe, and digestion with an enzyme which cuts the transposon once produces two fragments in the case of genuine Mu transposition. Genomic DNA from 17 kanMX4-Mu transposon integration yeast clones was isolated, digested with BamHI+BglII that do not cut the transposon sequence, or with HindIII that cleaves the transposon sequence once and analysed by Southern hybridisation with kanMX4 fragment as the probe. Fifteen isolates generated a single band with a discrete but different gel mobility after BamHI+BglII digestion (FIG. 4A) and two bands after HindIII digestion (FIG. 4B). Control DNA from the recipient strain FY1679 did not generate detectable bands in the analyses. Two isolates (G5 and G14) gave several hybridising fragments after BamHI+BglII digestion suggesting possibility of multiple transposon integrations. However, these two isolates gave three fragments after HindIII digestion, instead of doubling the amount of fragments detected in the BamHI+BglII digestion expected in case of multiple transposon integrations. The sizes of the HindIII fragments of the isolates G5 and G14 (4.3, 2.4 and 1.3 kb) and the pattern of bands in BamHI+BglII digestion suggested that the transposon was integrated into the yeast 2µ plasmid (for confirmation of this see sequencing results below). Genomic DNA from 17 G418-resistant isolates of the haploid strain FY-3 was analysed in a similar way after XhoI+SalI digestion (which do not cut the transposon) and PstI digestion (one cut in the transposon). Thirteen isolates gave one band after XhoI+SalI digestion and two bands after PstI digestion suggesting a single integration. Four isolates gave similar pattern of bands as isolates G5 and G14 of strain FY1679 suggesting integration into the 2µ plasmid (results not shown). These data indicate that in most of the studied clones the transposon DNA was integrated as a single copy into the yeast chromosome. In the rest of the clones a single integration was detected in an episome.

Seven mouse ES cell clones were analysed by Southern blotting. Their chromosomal DNA was digested with BamHI which releases almost an entire transposon from the genome. All the clones studied had a band at the same position as the BamHI digested pALH28 used as a control. The intensity of the band was similar for all clones studied and for control DNA representing same molar amount of DNA as the genomic samples. This suggests that only one copy of the transposon was integrated into each genome.

Figure 6:
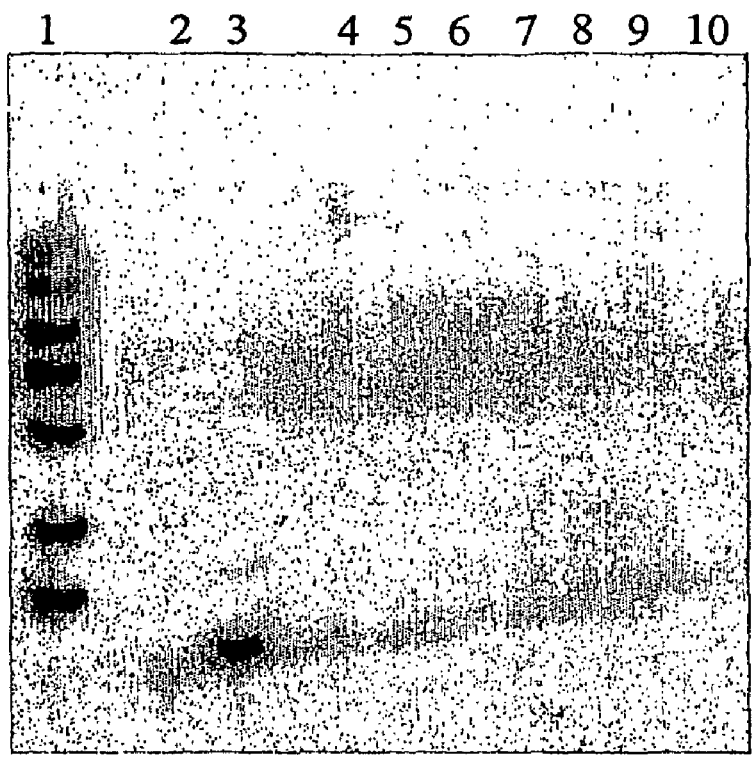
FIG. 6. Southern blot analysis of HeLa clones transfected with the transposon complexes. Lanes: 1. Marker with the following bands: 10 kb, 8 kb, 6 kb, 5 kb, 4 kb, 3 kb, 2.5 kb. 2. HeLa genomic DNA. 3. HeLa genomic DNA mixed with purified Mu/LoxP-Kan/Neo transposon (about 2.1 kb). HeLA clones: 4. RGC13 5. RGC14 6. RGC15 7. RGC16 8. RGC23 9. RGC24 10. RGC26

In HeLa cells, Southern blot analysis was used to confirm that the G418 resistant colonies had the transposon integrated into their genomes. Digestion of the genomic DNA with restriction enzyme(s) that do not cut the transposon produces one fragment hybridising to the transposon probe. Seven HeLa cell transfectant clones were analysed by Southern blot as shown in FIG. 6. Their chromosomal DNA was digested with NheI+SpeI which do not cut the transposon. A single band was detected from each of the clones indicating that a single copy of the transposon DNA has been integrated in each of the genomes.

The Location of Insertions in the Chromosomes

Figure 5A:
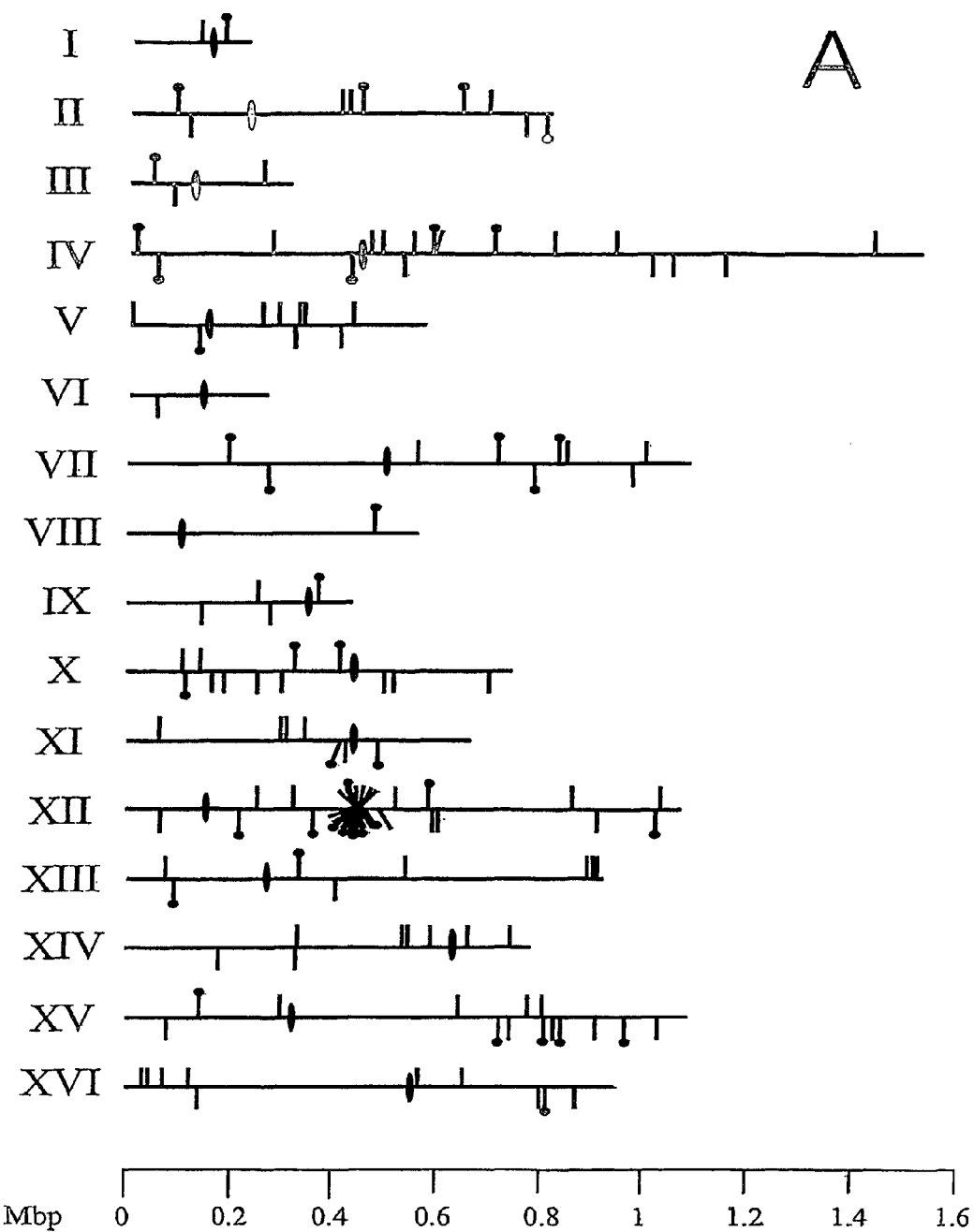
FIGS. 5A and 5B. Distribution of kanMX4-Mu integration sites on yeast chromosomes (5A) and in the repetitive rDNA region on chromosome 12 (5B). The ovals in (5A) designate the centromer of each chromosome. Integration sites in the diploid strain FY1679 are indicated by bars, and the integration sites in the haploid strain FY-3 by bars with filled circles. Above the line representing yeast genomic DNA are indicated the transposons that contained the kan gene in the orientation of Watson strand, below the line the transposons are in the Crick strand orientation.
Figure 5B:
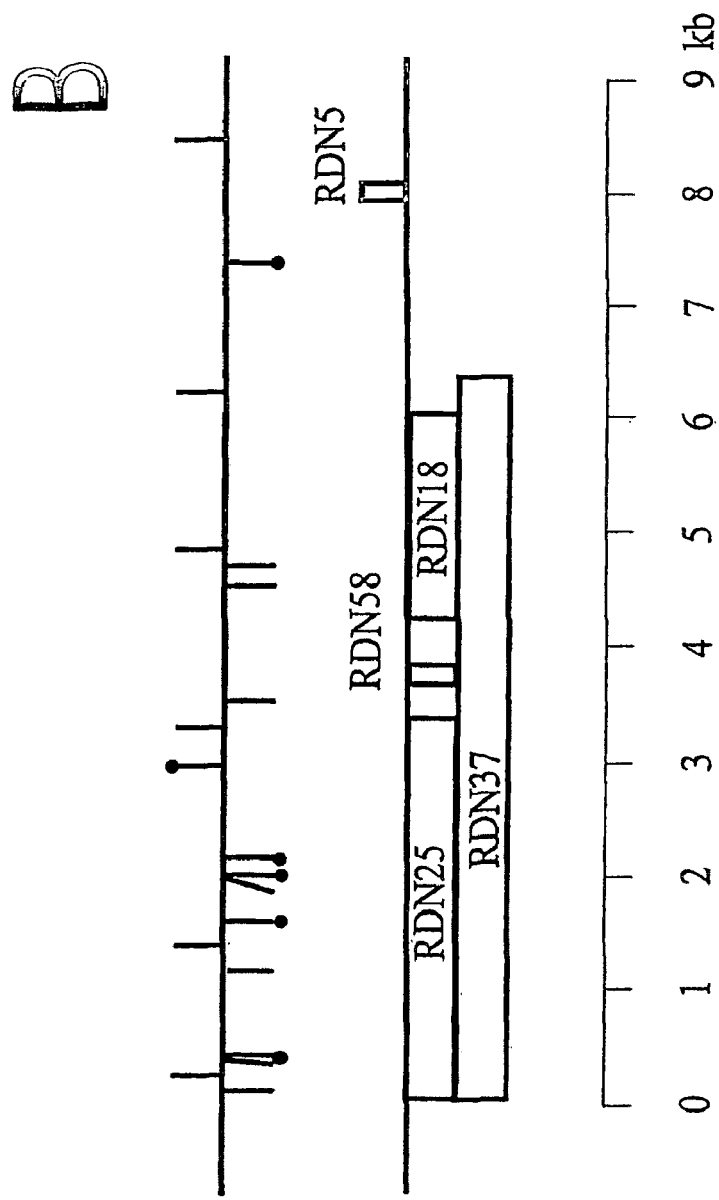

Yeast Mu transposons integrate almost randomly into the target DNA (Haapa-Paananen et al., 2002). To test the location and distribution of the transposon insertions we cloned transposon-genomic DNA borders from more than one hundred yeast transformants and sequenced the insertion sites on both sides of the transposon using transposon-specific primers (Seq A+Seq MX4). Exact mapping of the insertion sites was possible by BLAST comparison with the SGD database. We used the strain FY1679 which was used in the yeast whole genome sequencing (Winston et al. 1995) to ensure the correct mapping. The overall distribution of 140 integrations on the 16 chromosomes of the yeast is shown in FIG. 5A. All chromosomes were hit at least once. Both ORFs and intergenic regions had transposon integrations (Table 2). List of integrations into the genome is presented in Table 3. In the haploid genome, integrations on the essential genes were naturally missed due to the inviability of the cells. On chromosome XII there seems to be a real "hotspot" for transposon integration but this is an artefact since the "hotspot" is in the approximately 9 kb region encoding ribosomal RNA (FIG. 5B). This loci is repeated tandemly 100-200 times in the chromosome XII. In this region, the integrations are distributed randomly. The chromosomes in FIG. 5A are drawn according to SGD which shows only two copies of this repeated region (when the systematic sequencing of the yeast genome was done, only two rDNA repeats were sequenced) instead of 100 to 200 copies actually present in a yeast genome consisting of 1 to 2 Mb of DNA. Only nine integrations were found at a distance less than 1 kb from a tRNA gene which shows that Mu-transposon integration differs from that of Ty1-Ty4 elements. Integration closest to the end of a chromosome was 6.3 kb showing the difference to the telomere-preferring Ty5 element. The mean interval distance of insertions was 135 kb and was nowhere near covering the whole genome as a library. However, the distribution was even enough to show the randomness of the integration.

Mouse The sequenced transposon-genomic DNA borders were compared to the Mouse Genome Assembly v 3 using Ensembl Mouse Genome Server. The clone RGC57 contained an integrated transposon in the chromosome 3, duplicating positions 59433906-10, which are located in the last intron of both the ENSMUSESTG00000010433 and 10426. Sequencing showed presence of this 5-bp sequence (target site duplication) on both sides of the integrated transposon.

HeLa cells We cloned transposon-genomic DNA borders from three transfectants and sequenced the insertion sites on both sides of the transposon using transposon-specific primers (HSP 430 and HSP431). The integrations are presented in Table 5. All of these 3 transfectants had intact transposon ends with the 5 bp duplication of the target site at both sides of the transposon.

Integration of the Transposon in the Yeast 2µ Plasmid

Most *S. cerevisiae* strains contain an endogenous 2µ plasmid. The yeast 2µ plasmid is a 6318 bp circular species present extrachromosomally in *S. cerevisiae* at 60-100 copies per cell. The plasmid molecules are resident in the nucleus as minichromosomes with standard nucleosome phasing (Livingston and Hahne 1979; Nelson and Fangman 1979; Taketo et al., 1980).

In 23 clones out of 131 clones (17.6%) the transposon had integrated in the 2µ plasmid and in 108 clones (82.4%) the transposon had integrated into the chromosomes in the diploid strain FY1679. In the haploid strain FY-3, four clones out of 49 clones (8.2%) had the transposon in the 2µ plasmid and 45 clones (91.8%) had the transposon in the chromosomes.

Transposon Target Site

Genuine Mu transposition produces a 5-bp target site duplication flanking the integrated transposon (Haapa et al. 1999b). The transposon was flanked by target site duplication in 121 clones (out of 122; 99.2%) of the strain FY1679 and in 42 clones (out of 46; 91.3%) in the haploid strain FY-3 confirming that a majority of integrations were generated by DNA transposition chemistry. A consensus sequence of 5 bp duplication (5'-N-Y-G/C-R-N-3') has been observed in both in vivo and in vitro transposition reactions, the most preferred pentamers being 5'-C-Y-G/C-R-G-3' (Mizuuchi and Mizuuchi 1993; Haapa-Paananen et at. 2002; Butterfield et al. 2002). In this study, the distribution of nucleotides in duplicated pentamers agreed well with the previous results (Table 4).

TABLE 1

Number of geneticin-resistant colonies detected following electroporation of transpososomes into yeast strains, cfu/µg DNA

| DNA | FY1679 | FY-3 |
| --- | --- | --- |
| KanMX-Mu + MuA | 351 | 178 |
| KanMX-Mu − MuA | 0 | 1 |
| KanMX-p15A-Mu + MuA | 43 | 61 |
| KanMX-p15A-Mu − MuA | 0 | 0 |
| Plasmid pYC2/CT[a] | $6.9 \times 10^5$ | $5.6 \times 10^5$ |

[a]Electroporation of plasmid pYC2/CT DNA served as a control for competent status.

TABLE 2

Distribution of transposon integrations in FY1679 (diploid) and FY-3 (haploid) strains.

| Integration site | FY1679 | FY-3 | Total |
|---|---|---|---|
| Chromosomal DNA | | | |
| Protein coding region | | | 53 |
| Essential gene | 12 (1 intron) | 0 | |
| Nonessential gene | 29 | 11 | |
| rRNA | 12 | 7 | 19 |
| tRNA (intron) | 1 | 0 | 1 |
| Ty | 2 | 0 | 2 |
| Solo-LTR | 1 | 2 | 3 |
| Intergenic region | 48 | 23 | 71 |
| 2μ plasmid | | | |
| Protein coding region | 4 | 2 | 6 |
| Intergenic region | 12 | 2 | 14 |
| | 121 | 47 | 169 |

TABLE 3A

Transposon integration sites and target site duplications in *Saccharomyces cerevisiae* diploid strain FY1679.

| | ←seqmx4 | seqA→ | Location* | SEQ ID NO |
|---|---|---|---|---|
| G1 | caacatctagCTCAG(KanMX4-Mu) | CTCAGtgagttccga | chr13: 908424-908428 | 22 |
| G2 | agtactaccaTTGAA(KanMX4-Mu) | TTGAAtttacgttca | chr9: 279340-279344 | 23 |
| G3 | taaaaattcaGGCAT(KanMX4-Mu) | GGCATatacaattat | chr16: 569334-568338 | 24 |
| G4 | taaaccaccaTCTGT(KanMX4-Mu) | TCTGTcgcccatctt | chr12: 239388-239392 | 25 |
| G5 | ctgattactaGCGAA(KanMX4-Mu) | GCGAAgctgcgggtg | 2μ: 3447-3451(NC_001398) | 26 |
| G6 | aagaaaagctCAGTG(KanMX4-Mu) | AGTGgaataatttt | chr4: 825525-825529 | 27 |
| G7 | gaactctttcCCCAC(KanMX4-Mu) | CCCACcgatccattg | chr16: 862127-862131 | 28 |
| G8 | aaagatgaaaCCGAG(KanMX4-Mu) | CCGAGtaagctgcta | chr3: 263950-263954 | 29 |
| G9 | caatgcatcaTCTAC(KanMX4-Mu) | TCTACattacaaacc | chr2: 766314-766318 | 30 |
| G10 | tttgttcacgCGGGC(KanMX4-Mu) | CGGGCcgcagttgtg | chr11: 308515-308519 | 31 |
| G11 | atctgtattaACTTC(KanMX4-Mu) | ACTTCgaggtagtaa | chr7: 854983-854987 | 32 |
| G12 | tttttcatgttCCTAT(KanMX4-Mu) | CCTATtcttgttcct | chr5: 327111-327115 | 33 |
| G13 | tatccacttcTTAGA(KanMX4-Mu) | TTAGAgggactatcg | chr12: 456350-456354 | 34 |
| G14 | aaactgttttACAGA(KanMX4-Mu) | ACAGAtttacgatcg | 2μ: 2720-2724 | 35 |
| G15 | tggagttaggCTGGC(KanMX4-Mu) | CTGGCtcggactggc | chr10: 702930-702934 | 36 |
| G16 | gagcttctgcTTCAC(KanMX4-Mu) | TTCACgttttttgga | chr7: 568606-568610 | 37 |
| G17 | taacgctagaGGGGC(KanMX4-Mu) | GGGGCaagaaggaag | chr1: 136875-136879 | 38 |
| G18 | tccaaccgtaGTGGT(KanMX4-Mu) | GTGGTtatataataa | chr10: 241383-241387 | 39 |
| G19 | gggggcaatgGTGAA(KanMX4-Mu) | GTGAAatttcgacgc | chr4: 276367-276371 | 40 |
| G20 | taagagcttgTCCGC(KanMX4-Mu) | TCCGCttcgccccaa | chr13: 904363-904367 | 41 |
| G21 | cataagtgtaAGCCA(KanMX4-Mu) | AGCCAtatgttccct | chr9: 249583-249587 | 42 |
| G22 | tctggcttaaACCAG(KanMX4-Mu) | ACCAGcactatgtat | chr4: 544898-544902 | 43 |
| G23 | gttgaatcttCCGAT(KanMX4-Mu) | CCGATaccatcgaca | chr12: 65144-65148 | 44 |
| G34 | ccctagcgccTAGGG(KanMX4-Mu) | TAGGGtcgagtactg | chr9: 138283-138287 | 45 |
| G36 | ttgctttaacTAGGA(KanMX4-Mu) | TAGGAaagaataaga | chr15: 892270-892274 | 46 |
| G37 | agagactgaaGACGA(KanMX4-Mu) | GACGAggaaatcaaa | chr16: 67656-69660 | 47 |
| G38 | atggatggcgCTCAA(KanMX4-Mu) | CTCAAgcgtgttacc | chr12: 453865-453869 | 48 |
| G40 | tccatcttctGTGGA(KanMX4-Mu) | GTGGAgaagactcga | chr14: 661338-661342 | 49 |

TABLE 3A-continued

Transposon integration sites and target site duplications in *Saccharomyces cerevisiae* diploid strain FY1679.

| | ←seqmx4 seqA→ | | Location* | SEQ ID NO |
|---|---|---|---|---|
| G41 | ttcactcattCTGGT(KanMX4-Mu) | CTGGTcatttcttcg | chr15: 720163-720167 | 50 |
| G42 | ctagcgctttACGGA(KanMX4-Mu) | ACGGAagacaatgta | 2μ: 2838-2842 | 51 |
| G43 | ggtaataggcCCGTG(KanMX4-Mu) | CCGTGcggttccgtc | chr15: 836789-836793 | 52 |
| G44 | gtggtgccctTCCGT(KanMX4-Mu) | TCCGTcaattccttt | chr12: 456583-456587 | 53 |
| G45 | ttcgctgctcACCAA(KanMX4-Mu) | ACCAAtggaatcgca | chr12: 458164-458168 | 54 |
| G46 | aatattatctTCTGT(KanMX4-Mu) | TCTGTcattgttact | chr10: 135624-135628 | 55 |
| G47 | gtatgtacccACCGA(KanMX4-Mu) | ACCGAtgtagcagta | chr15: 829039-829043 | 56 |
| G48 | gttgatggtaCCTTG(KanMX4-Mu) | CCTTGacaccagcca | chr6: 44321-44325 | 57 |
| G49 | tacattgtctTCCGT(KanMX4-Mu) | TCCGTaaagcgctag | 2μ: 2838-2842 | 58 |
| G50 | ccgtggaagcCTCGC(KanMX4-Mu) | CTCGCccgatgagtt | chr10: 526881-526885 | 59 |
| G51 | tttcttttccTCCGC(KanMX4-Mu) | TCCGCttattgtat | chr12: 455126-455130 | 60 |
| G52 | gctgcgtctgACCAA(KanMX4-Mu) | ACCAAggccctcact | chr12: 453213-453217 | 61 |
| G53 | tactgttgaaCCGGG(KanMX4-Mu) | CCGGGtcgtacaact | chr14: 736161-736165 | 62 |
| G54 | caaatgtatcAGCAG(KanMX4-Mu) | AGCAGatgtacttcc | chr14: 566860-566864 | 63 |
| G55 | agtttccgctATAAA(KanMX4-Mu) | ATAAAtaatggcagc | chr10: 161496-161500 | 64 |
| G56 | aaaggaattgCTAGG(KanMX4-Mu) | CTAGGggcattactc | chr12: 912615-912619 | 65 |
| G57 | aaaaataattACTCT(KanMX4-Mu) | ACTCTaacatttctt | chr16: 120160-120164 | 66 |
| G58 | tgtttatatgATGAC(KanMX4-Mu) | ATGACgattttccca | chr11: 306835-306839 | 67 |
| G59 | ttgtgtattTTGAT(KanMX4-Mu) | TTGATtgaaaatgat | chr4: 600461-600465 | 68 |
| G60 | tatgataatcAAGGC(KanMX4-Mu) | AAGGCataattgact | chr2: 429112-429116 | 69 |
| G63 | cagcattaaaACGGC(KanMX4-Mu) | ACGGCagcaaagccc | chr16: 826635-826639 | 70 |
| G64 | ttgacatgtgATCTG(KanMX4-Mu) | ATCGTcacagatttt | 2μ: 5268-5272 | 71 |
| G65 | tcagctctcaGCAGA(KanMX4-Mu) | GCAGAgaaaaaattt | chr2: 117272-117276 | 72 |
| G66 | tgctaggtgtGTCTG(KanMX4-Mu) | GTCTGtttatgcatt | chr14: 331432-331436 | 73 |
| G67 | caattgaggtTTGAA(KanMX4-Mu) | TTGAAattgctggcc | chr.12: 455361-455365 | 74 |
| G67 | aatcatgcatTGCAT(KanMX4-Mu) | TGCATaatgtggtat | 2μ: 2196-2200 | 75 |
| G70 | acgatcttacGTCGG(KanMX4-Mu) | GTCGGctatctcacc | chr3: 77666-77670 | 76 |
| G71 | ttgtatttaaACTGG(KanMX4-Mu) | ACTGGagtgatttat | 2μ A: 5800-5804 | 77 |
| G74 | tgcatatttgCCTGC(KanMX4-Mu) | CCTGCgaaaaaaagt | chr5: 436799-436803 | 78 |
| G75 | tcgttgaataATGGA(KanMX4-Mu) | ATGGAaaatatgaaa | chr10: 187594-187598 | 79 |
| G76 | ctttcccagaACCAG(KanMX4-Mu) | ACCAGggaaactgtt | chr14: 537718-537722 | 80 |
| G77 | cctctgcatcCCAAC(KanMX4-Mu) | CCAACaccagcgata | chr4: 955105-955109 | 81 |
| G78 | atctgtaaacTCGCT(KanMX4-Mu) | TCGCTtgtgacgatg | chr4: 480341-480435 | 82 |
| G79 | tcctgcctaaACAGG(KanMX4-Mu) | ACAGGaagacaaagc | chr14: 547141-547145 | 83 |
| G80 | tagaaaaacCACAA(KanMX4-Mu) | CACAAcaacactatg | chr10: 111531-111535 | 84 |
| G81 | ttttggctcgTCCGG(KanMX4-Mu) | TCCGGatgatgcgaa | chr.16: 641397-641401 | 85 |
| G83 | tgtggctaccGCCCG(KanMX4-Mu) | GCCCGtgattcgggc | chr4: 1433822-1433826 | 86 |

TABLE 3A-continued

Transposon integration sites and target site duplications in *Saccharomyces cerevisiae* diploid strain FY1679.

|   | ←seqmx4     seqA→ | Location* | SEQ ID NO |
|---|---|---|---|
| G84 | ggcatagtgcGTGTT(KanMX4-Mu) GTGTTtatgcttaaa | 2μ: 541-545 | 87 |
| G85 | aaaatgcaacGCGAG(KanMX4-Mu) GCGAGagcgctaatt | 2μ: 3134-3138 | 88 |
| G87 | gaacagttccACGCC(KanMX4-Mu) ACGCCtgatatgagg | chr11: 60765-60769 | 89 |
| G88 | agcgcgactgCCCGA(KanMX4-Mu) CCCGAagaaggacgc | chr4: 1056229-1056233 | 90 |
| G90 | aaaaggttcaGTAGA(KanMX4-Mu) GTAGAaacataaaat | chr11: 430889-430893 | 91 |
| G94 | ccacaaggacGCCTT(KanMX4-Mu) GCCTTattcgtatcc | chr12: 451993-451997 | 92 |
| G96 | cagaatccatGCTAG(KanMX4-Mu) GCTAGaacgcggtga | chr12: 452043-452047 | 93 |
| G97 | cagctgctacCCAGG(KanMX4-Mu) CCAGGgattgccacg | chr2: 415433-415437 | 94 |
| G98 | ctagccgttcATCAA(KanMX4-Mu) ATCAAtcatgtcaaa | chr4: 539356-539360 | 95 |
| G99 | caaaaaagtcTAGAG(KanMX4-Mu) TAGAGgaaaaaaacg | chr13: 406197-406201 | 96 |
| G100 | ttgtcaaagtACCGA(KanMX4-Mu) ACCGAtcatgacaat | chr5: 258808-258812 | 97 |
| G101 | gtaacatcttGGGCG(KanMX4-Mu) GGGCGtttgcaacac | chr16: 135372-135376 | 98 |
| G102 | actgcctttgCTGAG(KanMX4-Mu) CTGAGctggatcaat | 2μ: 2524-2528 | 99 |
| G103 | aatgtaaaagGCAAG(KanMX4-Mu) GCAAGaaaacatgta | chr4: 1011940-1011944 | 100 |
| G104 | gcctgaattgTAGAT(KanMX4-Mu) TAGATattagataag | chr15: 770712-770716 | 101 |
| G105 | gtttgacattGTGAA(KanMX4-Mu) GTGAAgagacataga | chr12: 452744-452748 | 102 |
| G106 | tgtcatctacATCAT(KanMX4-Mu) ATCATcggtattatt | chr4: 1160847-1160851 | 103 |
| G107 | cttgttcctaGTGGC(KanMX4-Mu) GTGGCgctaatggga | chr4: 464844-464848 | 104 |
| G108 | agggccctcaGTGAT(KanMX4-Mu) GTGATggtgttttgt | 2μ B: 4396-4400 | 105 |
| G109 | ggtattttcaTTGGT(KanMX4-Mu) TTGGTtgtaaaatcg | chr12: 582690-582694 | 106 |
| G110 | caatctaaccACCAT(KanMX4-Mu) ACCATgttggctcac | chr15: 75760-75764 | 107 |
| G111 | cgaaaaatgcACCGG(KanMX4-Mu) ACCGGccgcgcatta | 2μ: 5427-5431 | 108 |
| G113 | ttacgatctgCTGAG(KanMX4-Mu) CTGAGattaagcctt | chr12: 451812-451816 | 109 |
| G114 | aaatcgagcaATCAC(KanMX4-Mu) GTGATtgctcgattt | 2μ: 2126-2130 | 110 |
| G116 | ccgacaaaccCCCCC(KanMX4-Mu) CCCCCcatttatata | chr15: 1039713-1039717 | 111 |
| G117 | caataagatgTGGGG(KanMX4-Mu) TGGGGattagtttcg | chr13: 895900-895904 | 112 |
| G118 | gtttaacgctTCCTG(KanMX4-Mu) TCCTGggaactgcag | chr16: 30277-30281 | 113 |
| G120 | atgaatactcCTCCC(KanMX4-Mu) CTCCCttgctgttgg | chr14: 175588-175592 | 114 |
| G121 | aatcacaatgGCGGC(KanMX4-Mu) GCGGCcatcgaccct | chr12: 1030933-1030937 | 115 |
| G122 | gagcaccacgATCGT(KanMX4-Mu) ATCGTtcggtgtact | chr13: 67812-67816 | 116 |
| G123 | aaaagcattcTGCAG(KanMX4-Mu) TGCAGtaattagccg | chr15: 638922-638926 | 117 |
| G124 | gtgattctccATGGG(KanMX4-Mu) ATGGGtggtttcgct | chr14: 333823-333827 | 118 |
| G125 | gctggtccagACCAC(KanMX4-Mu) ACCACaaaaggatgc | chr13: 540587-540591 | 119 |
| G126 | acttcgacttCGGGT(KanMX4-Mu) CGGGTaaaatactct | chr12: 328174-328178 | 120 |
| G127 | tgacattaatCCTAC(KanMX4-Mu) CCTACgtgacttaca | chr5: 291453-291457 | 121 |
| G128 | tttatatccgGTGGT(KanMX4-Mu) GTGGTtgcgataagg | chr5: 317469-317473 | 122 |
| G129 | ctgatgtgcgGTGGT(KanMX4-Mu) GTGGGccttggactt | chr5: 336404-336408 | 123 |

TABLE 3A-continued

Transposon integration sites and target site duplications in *Saccharomyces cerevisiae* diploid strain FY1679.

| | ←seqmx4   seqA→ | Location* | SEQ ID NO |
|---|---|---|---|
| G130 | gttgaactacTACGG(KanMX4-Mu)   TACGGttaagggtgc | chr16: 40318-40322 | 124 |
| G131 | cctatactctACCGT(KanMX4-Mu)   ACCGTcagggttgat | chr12: 453842-453846 | 125 |
| G132 | aactagcaaaATGGA(KanMX4-Mu)   ATGGAaacaaaaaaa | chr2: 692001-692005 | 126 |
| G133 | ttgactcaacACGGG(KanMX4-Mu)   ACGGGgaaactcacc | chr12: 456534-456538 | 127 |
| G134 | cattgtgaccCTGGC(KanMX4-Mu)   CTGGCaaatttgcaa | chr12: 651930-651934 | 128 |
| G135 | atacagctcaCTGTT(KanMX4-Mu)   CTGTTcacgtcgcac | 2µ B: 4039-4043 | 129 |
| G136 | tcagatttttCCCAG(KanMX4-Mu)   CCCAGtatggctttg | chr7: 976865-976869 | 130 |
| G137 | tttaacgtggGCGAA(KanMX4-Mu)   GCGAAgaagaaggaa | chr11: 327312-327316 | 131 |
| G138 | ccattccataTCTGT(KanMX4-Mu)   TCTGTtaagtataca | chr12: 460247-460251 | 132 |
| G140 | ctttgtgcgcTCTAT(KanMX4-Mu)   TCTATaatgcagtct | 2µ: 3318-3322 | 133 |
| G150 | aattggtacaGTATG(KanMX4-Mu)   GTATGctcaaaaata | chr12: 492584-492588 | 134 |
| T1 | ttgtagcttcCACAA(Mu-KanMX4-p15A-Mu)   CACAAgatgttggct | chr12: 645643-645647 | 135 |
| T2 | tcttattctcCTGTT(Mu-KanMX4-p15A-Mu)   CTGTTgccttcgtac | chr5: 7908-7912 | 136 |
| T3 | cggttgtataTGCAT(Mu-KanMX4-p15A-Mu)   TGCATtgtacgtgcg | chr5: 402750-402754 | 137 |
| T4 | ttttaataagGCAAT(Mu-KanMX4-p15A-Mu)   GCAATaatattaggt | chr10: 538071-538075 | 138 |
| T5 | tatcacttacTCGAA(Mu-KanMX4-p15A-Mu)   TCGAAcgttgacatt | chr12: 864259-864263 | 139 |
| T6 | aaagacatctACCGT(Mu-KanMX4-p15A-Mu)   ACCGTgaaggtgccg | chr7: 999996-1000000 | 140 |
| T7 | catattactgCCCGC(Mu-KanMX4-p15A-Mu)   CCCGCgtaatccaat | chr15: 304883-304887 | 141 |
| T8 | gtgttagtgaATGCC(Mu-KanMX4-p15A-Mu)   ATGCCtcaaactctt | chr10: 304087-304091 | 142 |

Target site duplication is typed in capital letters.
*Chromosome and the coordinates of the duplicated sequence.

TABLE 3B

Transposon integration sites and target site duplications in *Saccharomyces cerevisiae* haploid strain FY-3.

| | ←seqmx4   seqA→ | Location* | SEQ ID NO |
|---|---|---|---|
| G1 | aaagagaaaaATAAG(KanMX4-Mu)   ATAAGaaaatcttct | chr3: 38982-38986 | 143 |
| G2 | ccttttttcGTGGG(KanMX4-Mu)   GTGGGaaccgcttta | 2µ: A: 4372-4376 | 144 |
| G3 | atccacctttGCTGC(KanMX4-Mu)   (GCTGCttttccttaa) | 2µ: 5349-5353 | 145 |
| G4 | tacattcctcCTCAT(KanMX4-Mu)   CTCATttgaccgagg | chr16: 837554-837558 | 146 |
| G5 | gatttatcatGCAGT(KanMX4-Mu)   GCAGTaatactaata | chr4: 3069-3073 | 147 |
| G6 | gaattttaaGAGAtc(KanMX4-Mu)   GAtcAAgtcttgtga | chr15: 144910-144915 | 148 |
| G7 | gttcgatgctGTGCG(KanMX4-Mu)   GTGCGggacttctac | chr1: 191076-191080 | 149 |
| G8 | cttcacggtaACGTA(KanMX4-Mu)   ACGTAactgaatgtg | chr12: 453541-453545 | 150 |
| G9 | caaggagcagAGGGC(KanMX4-Mu)   AGGGCacaaaacacc | chr12: 454727-424731 | 151 |
| G10 | tcaataaacaGCCGA(KanMX4-Mu)   GCCGAcatacatccc | 2µ: 5123-5127 | 152 |
| G11 | gcgagatgagGTGAA(KanMX4-Mu)   GTGAAagaaacttta | chr7: 284048-284052 | 153 |

TABLE 3B-continued

Transposon integration sites and target site duplications in *Saccharomyces cerevisiae* haploid strain FY-3.

| | ←seqmx4 | seqA→ | Location* | SEQ ID NO |
|---|---|---|---|---|
| G12 | taaatttcatCCGGA(KanMX4-Mu) | CCGGAagaaaaatga | chr11: 489457-489461 | 154 |
| G13 | agaaaagtacAATTc(KanMX4-Mu) | gATcAaggttacggc | chr4: 56735-56740 | 155 |
| G14 | actgtcttttCCGGT(KanMX4-Mu) | CCGGTcattccaaca | chr11: 428648-428652 | 156 |
| G15 | atacacgctcATCAG(KanMX4-Mu) | ATCAGacaccacaaa | chr12: 453989-453993 | 157 |
| G16 | atagtatttcCTAGT(KanMX4-Mu) | CTAGTgatctcggcg | chr15: 989676-989680 | 158 |
| G17 | ttcctattctCTAGA(KanMX4-Mu) | CTAGAaagtatagga | 2μ: 704-708 | 159 |
| G28 | ttataaggttGTTTC(KanMX4-Mu) | gaGTTTCatatgtgttt | chr15: 854340-854344 | 160 |
| G37 | ttcgagagtgCCATT(KanMX4-Mu) | CCATTgtaccagact | chr8: 489155-489159 | 161 |
| G38 | atggatggcgCTCAA(KanMX4-Mu) | CTCAAgcgtgttacc | chr12: 453865-453869 | 162 |
| G39 | tccaaatgtaTTGTG(KanMX4-Mu) | TTGTGagatgaaaat | chr15: 834888-834892 | 163 |
| G40 | atgattatttCACGG(KanMX4-Mu) | CACGGatttcattag | chr13: 97657-97661 | 164 |
| G42 | atggaaaactAGCGC(KanMX4-Mu) | AGCGCataattttgt | chr4: 437081-437085 | 165 |
| G43 | gagaatcttgTCTTG(KanMX4-Mu) | TCTTGatgtaacaaa | chr7: 190765-190769 | 166 |
| G44 | tagcaaacgTAAGTCTtc(KanMX4-Mu) | gAAGTCTAAaggttgc | chr12: 459205-459213 | 167 |
| G45 | ttgccgcgaaGCTAC(KanMX4-Mu) | GCTACcatccgctgg | chr12: 452091-452095 | 168 |
| G46 | gtagctcttttTCCAT(KanMX4-Mu) | TCCATggatggacga | chr12: 645493-645497 | 169 |
| G47 | atgttcattcTCTGT(KanMX4-Mu) | TCTGTagcagtaaga | chr10: 337762-337766 | 170 |
| G48 | aatcgtaaccATAAA(KanMX4-Mu) | ATAAAtataagttcc | chr2: 806825-806829 | 171 |
| G49 | ccttcctgctGTGGG(KanMX4-Mu) | GTGGGcagagagcga | chr7: 739278-739278 | 172 |
| G50 | tcttagggttATTGG(KanMX4-Mu) | ATTGGtagggliittg | chr9: 382384-382388 | 173 |
| G51 | agttaacttcCCCGG(KanMX4-Mu) | CCCGGtgttcagtat | chr12: 1025073-1025077 | 174 |
| G52 | atgtgtcattGAGGG(KanMX4-Mu) | GAGGGaaaatgtaat | chr7: 798084-798088 | 175 |
| G53 | ggttaacttgCTCGC(KanMX4-Mu) | CTCGCcatatatatc | chr2: 657457-657461 | 176 |
| G54 | caaaaaaagaTGGAG(KanMX4-Mu) | TGGAGtacagtacgc | chr2: 466108-466112 | 177 |
| G55 | gatatttacgCTTAT(KanMX4-Mu) | CTTATcaatctctgg | chr2: 80588-80592 | 178 |
| G56 | gccgtggtttCCGGA(KanMX4-Mu) | CCGGAgaaagacgaa | chr13: 347229-347233 | 179 |
| G57 | tttctggaatTAGGG(KanMX4-Mu) | TAGGGtgacagaatg | chr4: 722468-722472 | 180 |
| G58 | attactttatTTGGC(KanMX4-Mu) | TTGGCtaaagatcct | chr4: 600407-600411 | 181 |
| G59 | cgttatcataTTGAT(KanMX4-Mu) | TTGAtattgcttatt | chr15: 696010-696013 | 182 |
| G60 | ggcaaactatCTCAC(KanMX4-Mu) | CTCACcagaggtctg | chr10: 117057-117061 | 183 |
| G61 | ctaatagtgcATGAT(KanMX4-Mu) | ATGATtatatatcaa | chr7: 853604-853608 | 184 |
| G62 | agaaattctcCTTGG(KanMX4-Mu) | CTTGGgattagataa | chr5: 137549-137553 | 185 |
| G63 | tcccgcactgGTGAT(KanMX4-Mu) | GTGATacctacaccc | chr12: 213298-213302 | 186 |
| G64 | atcattcattGCCGG(KanMX4-Mu) | GCCGGaaaagaaag | chr12: 370966-370970 | 187 |
| G65 | ctcacgctctGCGAT(KanMX4-Mu) | GCGATtaacagctca | chr10: 404834-404838 | 188 |

Target site duplication is typed in capital letters.
*Chromosome and the coordinates of the duplicated sequence.

TABLE 4

Nucleotide consensus of the sequenced duplicated pentamers. (Percentage)

| Nucleotide | 1 | 2 | 3 | 4 | 5 |
|---|---|---|---|---|---|
| FY1679 (n = 121): | | | | | |
| A | 34 (28) | 10 (8) | 13 (11) | 47 (39) | 27 (22) |
| C | 31 (26) | 58 (48) | 45 (37) | 8 (7) | 27 (22) |
| G | 28 (23) | 11 (9) | 49 (41) | 53 (44) | 36 (30) |
| T | 28 (23) | 42 (35) | 14 (12) | 13 (11) | 31 (26) |
| Consensus: | N | C/T | C/G | A/G | N |
| FY-3 (n = 42): | | | | | |
| A | 8 (19) | 3 (7) | 6 (14) | 15 (36) | 8 (19) |
| C | 14 (33) | 15 (36) | 11 (26) | 1 (2) | 7 (17) |
| G | 12 (28) | 3 (7) | 18 (42) | 22 (51) | 15 (35) |
| T | 8 (19) | 21 (50) | 7 (18) | 4 (10) | 12 (29) |
| Consensus: | N | C/T | C/G | A/G | N |
| FY1679 + FY-3 (n = 163): | | | | | |
| A | 42 (26) | 13 (8) | 19 (12) | 62 (38) | 35 (21) |
| C | 45 (28) | 73 (45) | 56 (34) | 9 (6) | 34 (21) |
| G | 40 (25) | 14 (9) | 67 (41) | 75 (46) | 51 (31) |
| T | 36 (22) | 63 (39) | 21 (13) | 17 (10) | 43 (26) |
| Consensus: | N | C/T | C/G | A/G | N |

TABLE 5

Transposon integration sites and target site duplications in HeLa cells.

| Clone | | Location* | SEQ ID NO |
|---|---|---|---|
| RGC16 | aggaggaagaACCAG(Mu/LoxP-Kan/Neo)ACCAGgcacatgctg | chr8: 128251032-128251036 | 189 |
| RGC26 | ttaaatgaacTTCAG(Mu/LoxP-Kan/Neo)TTCAGgaaaataatg | chr12: 15381980-15381984 | 190 |
| RGC35 | ccaatgagtcACCAG(Mu/LoxP-Kan/Neo)ACCAGaactgaacaa | chr2: 180174041-180174045 | 191 |

Target site duplication is typed in capital letters.
*Chromosome and the coordinates of the duplicated sequence.

REFERENCES

Allet, B. (1979). Mu insertion duplicates a 5 base pair sequence at the host inserted site. Cell 1, 123-129.

Ausubel, F. M., Brent, R., Kingston, R. E., Moore, D. D., Seidman, J. G., Smith, J. A., and Struhl, K. (1989). Current protocols in molecular biology. John Wiley & Sons, New York, N.Y.

Behrens, R., Hayles, J., and Nurse, P. (2000). Fission yeast retrotransposon Tf1 integration is targeted to 5' ends of open reading frames. Nucleic Acids Res. 23, 4709-4716.

Butterfield, Y. S., Marra, M. A., Asano, J. K., Chan, S. Y., Guin, R., Krzywinski, M. I., Lee, S. S., MacDonald, K. W., Mathewson, C. A., and Olson, T. E. et al. (2002). An efficient strategy for large-scale high-throughput transposon-mediated sequencing of cDNA clones. Nucleic Acids Res. 11, 2460-2468.

Chaconas, G., Lavoie, B. D., and Watson, M. A. (1996). DNA transposition: jumping gene machine, some assembly required. Curr. Biol. 7, 817-820.

Haapa, S., Suomalainen, S., Eerikainen, S., Airaksinen, M., Paulin, L., and Savilahti, H. (1999a). An efficient DNA sequencing strategy based on the bacteriophage mu in vitro DNA transposition reaction. Genome Res. 3, 308-315.

Haapa, S., Taira, S., Heikkinen, E., and Savilahti, H. (1999b). An efficient and accurate integration of mini-Mu transposons in vitro: a general methodology for functional genetic analysis and molecular biology applications. Nucleic Acids Res. 13, 2777-2784.

Haapa-Paananen, S., Rita, H., and Savilahti, H. (2002). DNA transposition of bacteriophage Mu. A quantitative analysis of target site selection in vitro. J. Biol. Chem. 4, 2843-2851.

Ji, H., Moore, D. P., Blomberg, M. A., Braiterman, L. T., Voytas, D. F., Natsoulis, G., and Boeke, J. D. (1993). Hotspots for unselected Ty1 transposition events on yeast chromosome III are near tRNA genes and LTR sequences. Cell 5, 1007-1018.

Kahmann, R., and Kamp, D. (1979). Nucleotide sequences of the attachment sites of bacteriophage Mu DNA. Nature 5719, 247-250.

Kekarainen, T., Savilahti, H., and Valkonen, J. P. (2002). Functional genomics on potato virus A: virus genome-wide map of sites essential for virus propagation. Genome Res. 4, 584-594.

Lamberg, A., Nieminen, S., Qiao, M., and Savilahti, H. (2002). Efficient insertion mutagenesis strategy for bacterial genomes involving electroporation of in vitro-assembled DNA transposition complexes of bacteriophage mu. Appl. Environ. Microbiol. 2, 705-712.

Laurent, L. C., Olsen, M. N., Crowley, R. A., Savilahti, H., and Brown, P. O. (2000). Functional characterization of the human immunodeficiency virus type 1 genome by genetic footprinting. J. Virol. 6, 2760-2769.

Livingston, D. M., and Hahne, S. (1979). Isolation of a condensed, intracellular form of the 2-micrometer DNA plasmid of Saccharomyces cerevisiae. Proc. Natl. Acad. Sci. U.S.A. 8, 3727-3731.

Miller, S. A., Dykes, D. D., and Polesky, H. F. (1988). A simple salting out procedure for extracting DNA from human nucleated cells. Nucleic Acids Res. 3, 1215.

Mizuuchi, K. (1992). Transpositional recombination: mechanistic insights from studies of mu and other elements. Annu. Rev. Biochem. 1011-1051.

Mizuuchi, M., and Mizuuchi, K. (1993). Target site selection in transposition of phage Mu. Cold Spring Harb. Symp. Quant. Biol. 515-523.

Nelson, R. G., and Fangman, W. L. (1979). Nucleosome organization of the yeast 2-micrometer DNA plasmid: a eukaryotic minichromosome. Proc. Natl. Acad. Sci. U.S.A. 12, 6515-6519.

Raz, E., van Luenen, H. G. A. M., Schaerringer, B., Plasterk, R. H. A., and Driever, W. (1997). Transposition of the nematode Caenohabditis elegans Tc3 element in the zebrafish Danio rerio. Current Biology 8, 82-88.

Rose, R. E. (1988). The nucleotide sequence of pACYC184. Nucleic Acids Res. 1, 355.

Rubin, G. M., and Spradling, A. C. (1982). Genetic transformation of Drosophila with transposable element vectors. Science 218, 348-353.

Sambrook, J., Fritch, E. F., and Maniatis, T. (1989). Molecular cloning: a laboratory manual, 2$^{nd}$ ed. Cold Spring Harbor Laboratory Press, Cold Spring Harbor, N.Y.

Sands, A. T., and Hasty, E. P. eds. (1997). Mouse mutagenesis, Lexicon Genetics Incorporated: Houston, Tex.

Savilahti, H., and Mizuuchi, K. (1996). Mu transpositional recombination: donor DNA cleavage and strand transfer in trans by the Mu transposase. Cell 2, 271-280.

Savilahti, H., Rice, P. A. and Mizuuchi, K. (1995) The phage Mu transpososome core: DNA requirements for assembly and function. EMBO J. 14, 4893-4903

Sherman, F., Fink, G. R. and Lawrence, C. W. (1981) Methods in yeast genetics. Cold Spring Harbor Laboratory Press, Cold Spring Harbor, N.Y.

Taira, S., Tuimala, J., Roine, E., Nurmiaho-Lassila, E. L., Savilahti, H., and Romantschuk, M. (1999). Mutational analysis of the *Pseudomonas syringae* pv. tomato hrpA gene encoding Hrp pilus subunit. Mol. Microbiol. 4, 737-744.

Taketo, M., Jazwinski, S. M., and Edelman, G. M. (1980). Association of the 2-micron DNA plasmid with yeast folded chromosomes. Proc. Natl. Acad. Sci. U.S.A. 6, 3144-3148.

Vilen, H., Eerikainen, S., Tornberg, J., Airaksinen, M. S., and Savilahti, H. (2001). Construction of gene-targeting vectors: a rapid Mu in vitro DNA transposition-based strategy generating null, potentially hypomorphic, and conditional alleles. Transgenic Res. 1, 69-80.

Vilen, H., Aalto, J-M., Kassinen, A., Paulin, L., and Savilahti, H. (2003). A direct transposon insertion tool for modification and functional analysis of viral genomes. J. Virol. 77, 123-134.

Wach, A., Brachat, A., Pohlmann, R., and Philippsen, P. (1994). New heterologous modules for classical or PCR-based gene disruptions in *Saccharomyces cerevisiae*. Yeast 13, 1793-1808.

Winston, F., Dollard, C., and Ricupero-Hovasse, S. L. (1995). Construction of a set of convenient *Saccharomyces cerevisiae* strains that are isogenic to S288C. Yeast 1, 53-55.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

What is claimed is:

1. A method for incorporating nucleic acid segments into cellular nucleic acid of an isolated eukaryotic target cell, the method comprising
    delivering into the eukaryotic target cell an in vitro assembled Mu transposition complex that comprises (i) MuA transposases and (ii) a transposon segment that comprises a pair of Mu end sequences recognized and bound by MuA transposase and an insert sequence between the Mu end sequences, wherein the transposon segment is integrated by transposition into the cellular nucleic acid of the target cell and the integration is mediated by MuA only, and wherein the eukaryotic target cell excludes mammalian cells.

2. The method of claim 1, wherein the Mu transposition complex is delivered into the target cell by electroporation or micro-injection.

3. The method of claim 1, wherein the nucleic acid segment is incorporated to a random or substantially random position of the cellular nucleic acid of the target cell.

4. The method of claim 1, wherein the nucleic acid segment is incorporated to a targeted position of the cellular nucleic acid of the target cell.

5. The method of claim 1, wherein the target cell is a plant, fish, fungi or yeast cell.

6. The method of claim 1, wherein the eukaryotic target cell is a stem cell.

7. The method of claim 1, wherein the insert sequence comprises a marker, which is selectable in eukaryotic cells.

8. The method of claim 1, wherein a concentrated fraction of Mu transposition complexes is are delivered into the target cell.

9. The method of claim 1 further comprising the step of incubating the target cells under conditions that promote transposition into the cellular nucleic acid.

10. A method for incorporating nucleic acid segments into cellular nucleic acid of an isolated plant target cell, the method comprising
    delivering into the plant target cell an in vitro assembled Mu transposition complex that comprises (i) MuA transposases and (ii) a transposon segment that comprises a pair of Mu end sequences recognized and bound by MuA transposase and an insert sequence between said Mu end sequences, wherein the transposon segment is integrated by transposition into the cellular nucleic acid of the target cell and the integration is mediated by MuA only.

11. A method for incorporating nucleic acid segments into cellular nucleic acid of an isolated fish target cell, the method comprising
    delivering into the fish target cell an in vitro assembled Mu transposition complex that comprises (i) MuA transposases and (ii) a transposon segment that comprises a pair of Mu end sequences recognized and bound by MuA transposase and an insert sequence between said Mu end sequences, wherein the transposon segment is integrated by transposition into the cellular nucleic acid of the target cell and the integration is mediated by MuA only.

12. A method for forming an insertion mutant library from a pool of eukaryotic target cells, the method comprising
    delivering into a eukaryotic target cell an in vitro assembled Mu transposition complex that comprises (i) MuA transposases and (ii) a transposon segment that comprises a pair of Mu end sequences recognized and bound by MuA transposase and an insert sequence with a selectable marker between the Mu end sequences, wherein the transposon segment is integrated by transposition into a cellular nucleic acid of the target cell and the integration is mediated by MuA only; and
    screening for target cells that comprise the selectable marker, wherein the eukaryotic target cell excludes mammalian cells.

* * * * *

UNITED STATES PATENT AND TRADEMARK OFFICE
CERTIFICATE OF CORRECTION

PATENT NO.         : 8,192,934 B2
APPLICATION NO.    : 13/229258
DATED              : June 5, 2012
INVENTOR(S)        : Savilahti et al.

It is certified that error appears in the above-identified patent and that said Letters Patent is hereby corrected as shown below:

Title Page, Item (75): Inventor "Hikka Turakainen" should read --Hilkka Turakainen--

Claim 8, Col. 79, Line 40 "is are" should read --is--

Signed and Sealed this
Fourteenth Day of August, 2012

David J. Kappos
*Director of the United States Patent and Trademark Office*

```
                        SEQUENCE LISTING

<160> NUMBER OF SEQ ID NOS: 191

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 1
gctctccccg tggaggtaat                                           20

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 2
ttccgtcaca ggtatttatt cggt                                      24

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 3
atcagcggcc gcgatcc                                              17

<210> SEQ ID NO 4
<211> LENGTH: 20
<212> TYPE: DNA
<213> ORGANISM: Artificial Sequence
<220> FEATURE:
```

```
<223> OTHER INFORMATION: Description of Artificial Sequence:
      Oligonucleotide primer

<400> SEQUENCE: 4
ggacgaggca agctaaacag                                              20

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 5
ctaataccac tcacataggg cggccgcccg ggc                                33

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 6
gatcgcccgg gcg                                                     13

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 7
ctaggcccgg gcg                                                     13

<210> SEQ ID NO 8
<211> LENGTH: 13
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 8
aattgcccgg gcg                                                     13

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 9
ctaataccac tcacataggg                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer
```

```
<400> SEQUENCE: 10
gggcggccgc ccgggcgatc                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 11
gggcggccgc ccgggcctag                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 12
gggcggccgc ccgggcaatt                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 13
ctgtcgattc gatactaacg                                              20

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 14
ctctagatga tcagcggccg cgatccg                                      27

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 15
tgtcaaggag ggtattctgg                                              20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 16
```

-continued

```
ggtgacccgg cggggacgag gc                                      22
```

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 17

```
gatccgtttt cgcatttatc gtg                                     23
```

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 18

```
ggccgcatcg ataagcttgg gctgcagg                                28
```

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 19

```
acattgggtg gaaacattcc                                         20
```

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 20

```
ccaagttcgg gtgaaggc                                           18
```

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 21

```
ccccgggcga gtctagggcc gc                                      22
```

<210> SEQ ID NO 22
<211> LENGTH: 30
<212> TYPE: DNA
<213> ORGANISM: Saccharomyces cerevisiae

<400> SEQUENCE: 22

```
caacatctag ctcagctcag tgagttccga                              30
```

<210> SEQ ID NO 23

```
<211> LENGTH: 30
<212> TYPE: DNA
<213> ORGANISM: Saccharomyces cerevisiae

<400> SEQUENCE: 23
agtactacca ttgaattgaa tttacgttca                                   30

<210> SEQ ID NO 24
<211> LENGTH: 30
<212> TYPE: DNA
<213> ORGANISM: Saccharomyces cerevisiae

<400> SEQUENCE: 24
taaaaattca ggcatggcat atacaattat                                   30

<210> SEQ ID NO 25
<211> LENGTH: 30
<212> TYPE: DNA
<213> ORGANISM: Saccharomyces cerevisiae

<400> SEQUENCE: 25
taaaccacca tctgttctgt cgcccatctt                                   30

<210> SEQ ID NO 26
<211> LENGTH: 30
<212> TYPE: DNA
<213> ORGANISM: Saccharomyces cerevisiae

<400> SEQUENCE: 26
ctgattacta gcgaagcgaa gctgcgggtg                                   30

<210> SEQ ID NO 27
<211> LENGTH: 30
<212> TYPE: DNA
<213> ORGANISM: Saccharomyces cerevisiae

<400> SEQUENCE: 27
aagaaaagct cagtgcagtg gaataatttt                                   30

<210> SEQ ID NO 28
<211> LENGTH: 30
<212> TYPE: DNA
<213> ORGANISM: Saccharomyces cerevisiae

<400> SEQUENCE: 28
gaactctttc cccaccccac cgatccattg                                   30

<210> SEQ ID NO 29
<211> LENGTH: 30
<212> TYPE: DNA
<213> ORGANISM: Saccharomyces cerevisiae

<400> SEQUENCE: 29
aaagatgaaa ccgagccgag taagctgcta                                   30

<210> SEQ ID NO 30
<211> LENGTH: 30
<212> TYPE: DNA
<213> ORGANISM: Saccharomyces cerevisiae

<400> SEQUENCE: 30
caatgcatca tctactctac attacaaacc                                   30

<210> SEQ ID NO 31
```

```
<211> LENGTH: 30
<212> TYPE: DNA
<213> ORGANISM: Saccharomyces cerevisiae

<400> SEQUENCE: 31
tttgttcacg cgggccgggc cgcagttgtg                               30

<210> SEQ ID NO 32
<211> LENGTH: 30
<212> TYPE: DNA
<213> ORGANISM: Saccharomyces cerevisiae

<400> SEQUENCE: 32
atctgtatta acttcacttc gaggtagtaa                               30

<210> SEQ ID NO 33
<211> LENGTH: 30
<212> TYPE: DNA
<213> ORGANISM: Saccharomyces cerevisiae

<400> SEQUENCE: 33
ttttcatgtt cctatcctat tcttgttctt                               30

<210> SEQ ID NO 34
<211> LENGTH: 30
<212> TYPE: DNA
<213> ORGANISM: Saccharomyces cerevisiae

<400> SEQUENCE: 34
tatccacttc ttagattaga gggactatcg                               30

<210> SEQ ID NO 35
<211> LENGTH: 30
<212> TYPE: DNA
<213> ORGANISM: Saccharomyces cerevisiae

<400> SEQUENCE: 35
aaactgtttt acagaacaga tttacgatcg                               30

<210> SEQ ID NO 36
<211> LENGTH: 30
<212> TYPE: DNA
<213> ORGANISM: Saccharomyces cerevisiae

<400> SEQUENCE: 36
tggagttagg ctggcctggc tcggactggc                               30

<210> SEQ ID NO 37
<211> LENGTH: 30
<212> TYPE: DNA
<213> ORGANISM: Saccharomyces cerevisiae

<400> SEQUENCE: 37
gagcttctgc ttcacttcac gttttttgga                               30

<210> SEQ ID NO 38
<211> LENGTH: 30
<212> TYPE: DNA
<213> ORGANISM: Saccharomyces cerevisiae

<400> SEQUENCE: 38
taacgctaga ggggcggggc aagaaggaag                               30

<210> SEQ ID NO 39
```

```
<211> LENGTH: 30
<212> TYPE: DNA
<213> ORGANISM: Saccharomyces cerevisiae

<400> SEQUENCE: 39
tccaaccgta gtggtgtggt tatataataa                              30

<210> SEQ ID NO 40
<211> LENGTH: 30
<212> TYPE: DNA
<213> ORGANISM: Saccharomyces cerevisiae

<400> SEQUENCE: 40
gggggcaatg gtgaagtgaa atttcgacgc                              30

<210> SEQ ID NO 41
<211> LENGTH: 30
<212> TYPE: DNA
<213> ORGANISM: Saccharomyces cerevisiae

<400> SEQUENCE: 41
taagagcttg tccgctccgc ttcgccccaa                              30

<210> SEQ ID NO 42
<211> LENGTH: 30
<212> TYPE: DNA
<213> ORGANISM: Saccharomyces cerevisiae

<400> SEQUENCE: 42
cataagtgta agccaagcca tatgttccct                              30

<210> SEQ ID NO 43
<211> LENGTH: 30
<212> TYPE: DNA
<213> ORGANISM: Saccharomyces cerevisiae

<400> SEQUENCE: 43
tctggcttaa accagaccag cactatgtat                              30

<210> SEQ ID NO 44
<211> LENGTH: 30
<212> TYPE: DNA
<213> ORGANISM: Saccharomyces cerevisiae

<400> SEQUENCE: 44
gttgaatctt ccgatccgat accatcgaca                              30

<210> SEQ ID NO 45
<211> LENGTH: 30
<212> TYPE: DNA
<213> ORGANISM: Saccharomyces cerevisiae

<400> SEQUENCE: 45
ccctagcgcc tagggtaggg tcgagtactg                              30

<210> SEQ ID NO 46
<211> LENGTH: 30
<212> TYPE: DNA
<213> ORGANISM: Saccharomyces cerevisiae

<400> SEQUENCE: 46
ttgctttaac taggatagga aagaataaga                              30

<210> SEQ ID NO 47
```

```
<211> LENGTH: 30
<212> TYPE: DNA
<213> ORGANISM: Saccharomyces cerevisiae

<400> SEQUENCE: 47
agagactgaa gacgagacga ggaaatcaaa                                    30

<210> SEQ ID NO 48
<211> LENGTH: 30
<212> TYPE: DNA
<213> ORGANISM: Saccharomyces cerevisiae

<400> SEQUENCE: 48
atggatggcg ctcaactcaa gcgtgttacc                                    30

<210> SEQ ID NO 49
<211> LENGTH: 30
<212> TYPE: DNA
<213> ORGANISM: Saccharomyces cerevisiae

<400> SEQUENCE: 49
tccatcttct gtggagtgga gaagactcga                                    30

<210> SEQ ID NO 50
<211> LENGTH: 30
<212> TYPE: DNA
<213> ORGANISM: Saccharomyces cerevisiae

<400> SEQUENCE: 50
ttcactcatt ctggtctggt catttcttcg                                    30

<210> SEQ ID NO 51
<211> LENGTH: 30
<212> TYPE: DNA
<213> ORGANISM: Saccharomyces cerevisiae

<400> SEQUENCE: 51
ctagcgcttt acggaacgga agacaatgta                                    30

<210> SEQ ID NO 52
<211> LENGTH: 30
<212> TYPE: DNA
<213> ORGANISM: Saccharomyces cerevisiae

<400> SEQUENCE: 52
ggtaataggc ccgtgccgtg cggttccgtc                                    30

<210> SEQ ID NO 53
<211> LENGTH: 30
<212> TYPE: DNA
<213> ORGANISM: Saccharomyces cerevisiae

<400> SEQUENCE: 53
gtggtgccct tccgttccgt caattccttt                                    30

<210> SEQ ID NO 54
<211> LENGTH: 30
<212> TYPE: DNA
<213> ORGANISM: Saccharomyces cerevisiae

<400> SEQUENCE: 54
ttcgctgctc accaaaccaa tggaatcgca                                    30

<210> SEQ ID NO 55
```

```
<211> LENGTH: 30
<212> TYPE: DNA
<213> ORGANISM: Saccharomyces cerevisiae

<400> SEQUENCE: 55
aatattatct tctgttctgt cattgttact                                   30

<210> SEQ ID NO 56
<211> LENGTH: 30
<212> TYPE: DNA
<213> ORGANISM: Saccharomyces cerevisiae

<400> SEQUENCE: 56
gtatgtaccc accgaaccga tgtagcagta                                   30

<210> SEQ ID NO 57
<211> LENGTH: 30
<212> TYPE: DNA
<213> ORGANISM: Saccharomyces cerevisiae

<400> SEQUENCE: 57
gttgatggta ccttgccttg acaccagcca                                   30

<210> SEQ ID NO 58
<211> LENGTH: 30
<212> TYPE: DNA
<213> ORGANISM: Saccharomyces cerevisiae

<400> SEQUENCE: 58
tacattgtct tccgttccgt aaagcgctag                                   30

<210> SEQ ID NO 59
<211> LENGTH: 30
<212> TYPE: DNA
<213> ORGANISM: Saccharomyces cerevisiae

<400> SEQUENCE: 59
ccgtggaagc ctcgcctcgc ccgatgagtt                                   30

<210> SEQ ID NO 60
<211> LENGTH: 30
<212> TYPE: DNA
<213> ORGANISM: Saccharomyces cerevisiae

<400> SEQUENCE: 60
tttcttttcc tccgctccgc ttattgatat                                   30

<210> SEQ ID NO 61
<211> LENGTH: 30
<212> TYPE: DNA
<213> ORGANISM: Saccharomyces cerevisiae

<400> SEQUENCE: 61
gctgcgtctg accaaaccaa ggccctcact                                   30

<210> SEQ ID NO 62
<211> LENGTH: 30
<212> TYPE: DNA
<213> ORGANISM: Saccharomyces cerevisiae

<400> SEQUENCE: 62
tactgttgaa ccgggccggg tcgtacaact                                   30

<210> SEQ ID NO 63
```

-continued

```
<211> LENGTH: 30
<212> TYPE: DNA
<213> ORGANISM: Saccharomyces cerevisiae

<400> SEQUENCE: 63
caaatgtatc agcagagcag atgtacttcc                                    30

<210> SEQ ID NO 64
<211> LENGTH: 30
<212> TYPE: DNA
<213> ORGANISM: Saccharomyces cerevisiae

<400> SEQUENCE: 64
agtttccgct ataaaataaa taatggcagc                                    30

<210> SEQ ID NO 65
<211> LENGTH: 30
<212> TYPE: DNA
<213> ORGANISM: Saccharomyces cerevisiae

<400> SEQUENCE: 65
aaaggaattg ctaggctagg ggcattactc                                    30

<210> SEQ ID NO 66
<211> LENGTH: 30
<212> TYPE: DNA
<213> ORGANISM: Saccharomyces cerevisiae

<400> SEQUENCE: 66
aaaaataatt actctactct aacatttctt                                    30

<210> SEQ ID NO 67
<211> LENGTH: 30
<212> TYPE: DNA
<213> ORGANISM: Saccharomyces cerevisiae

<400> SEQUENCE: 67
tgtttatatg atgacatgac gattttccca                                    30

<210> SEQ ID NO 68
<211> LENGTH: 30
<212> TYPE: DNA
<213> ORGANISM: Saccharomyces cerevisiae

<400> SEQUENCE: 68
ttgtgtattt ttgatttgat tgaaaatgat                                    30

<210> SEQ ID NO 69
<211> LENGTH: 30
<212> TYPE: DNA
<213> ORGANISM: Saccharomyces cerevisiae

<400> SEQUENCE: 69
tatgataatc aaggcaaggc ataattgact                                    30

<210> SEQ ID NO 70
<211> LENGTH: 30
<212> TYPE: DNA
<213> ORGANISM: Saccharomyces cerevisiae

<400> SEQUENCE: 70
cagcattaaa acggcacggc agcaaagccc                                    30

<210> SEQ ID NO 71
```

```
<211> LENGTH: 30
<212> TYPE: DNA
<213> ORGANISM: Saccharomyces cerevisiae

<400> SEQUENCE: 71
ttgacatgtg atctgatcgt cacagatttt                              30

<210> SEQ ID NO 72
<211> LENGTH: 30
<212> TYPE: DNA
<213> ORGANISM: Saccharomyces cerevisiae

<400> SEQUENCE: 72
tcagctctca gcagagcaga gaaaaaattt                              30

<210> SEQ ID NO 73
<211> LENGTH: 30
<212> TYPE: DNA
<213> ORGANISM: Saccharomyces cerevisiae

<400> SEQUENCE: 73
tgctaggtgt gtctggtctg tttatgcatt                              30

<210> SEQ ID NO 74
<211> LENGTH: 30
<212> TYPE: DNA
<213> ORGANISM: Saccharomyces cerevisiae

<400> SEQUENCE: 74
caattgaggt ttgaattgaa attgctggcc                              30

<210> SEQ ID NO 75
<211> LENGTH: 30
<212> TYPE: DNA
<213> ORGANISM: Saccharomyces cerevisiae

<400> SEQUENCE: 75
aatcatgcat tgcattgcat aatgtggtat                              30

<210> SEQ ID NO 76
<211> LENGTH: 30
<212> TYPE: DNA
<213> ORGANISM: Saccharomyces cerevisiae

<400> SEQUENCE: 76
acgatcttac gtcgggtcgg ctatctcacc                              30

<210> SEQ ID NO 77
<211> LENGTH: 30
<212> TYPE: DNA
<213> ORGANISM: Saccharomyces cerevisiae

<400> SEQUENCE: 77
ttgtatttaa actggactgg agtgatttat                              30

<210> SEQ ID NO 78
<211> LENGTH: 30
<212> TYPE: DNA
<213> ORGANISM: Saccharomyces cerevisiae

<400> SEQUENCE: 78
tgcatatttg cctgccctgc gaaaaaaagt                              30

<210> SEQ ID NO 79
```

```
<211> LENGTH: 30
<212> TYPE: DNA
<213> ORGANISM: Saccharomyces cerevisiae

<400> SEQUENCE: 79
tcgttgaata atggaatgga aaatatgaaa                                    30

<210> SEQ ID NO 80
<211> LENGTH: 30
<212> TYPE: DNA
<213> ORGANISM: Saccharomyces cerevisiae

<400> SEQUENCE: 80
ctttcccaga accagaccag ggaaactgtt                                    30

<210> SEQ ID NO 81
<211> LENGTH: 30
<212> TYPE: DNA
<213> ORGANISM: Saccharomyces cerevisiae

<400> SEQUENCE: 81
cctctgcatc ccaacccaac accagcgata                                    30

<210> SEQ ID NO 82
<211> LENGTH: 30
<212> TYPE: DNA
<213> ORGANISM: Saccharomyces cerevisiae

<400> SEQUENCE: 82
atctgtaaac tcgcttcgct tgtgacgatg                                    30

<210> SEQ ID NO 83
<211> LENGTH: 30
<212> TYPE: DNA
<213> ORGANISM: Saccharomyces cerevisiae

<400> SEQUENCE: 83
tcctgcctaa acaggacagg aagacaaagc                                    30

<210> SEQ ID NO 84
<211> LENGTH: 30
<212> TYPE: DNA
<213> ORGANISM: Saccharomyces cerevisiae

<400> SEQUENCE: 84
tagaaaaaac cacaacacaa caacactatg                                    30

<210> SEQ ID NO 85
<211> LENGTH: 30
<212> TYPE: DNA
<213> ORGANISM: Saccharomyces cerevisiae

<400> SEQUENCE: 85
ttttggctcg tccggtccgg atgatgcgaa                                    30

<210> SEQ ID NO 86
<211> LENGTH: 30
<212> TYPE: DNA
<213> ORGANISM: Saccharomyces cerevisiae

<400> SEQUENCE: 86
tgtggctacc gcccggcccg tgattcgggc                                    30

<210> SEQ ID NO 87
```

```
<211> LENGTH: 30
<212> TYPE: DNA
<213> ORGANISM: Saccharomyces cerevisiae

<400> SEQUENCE: 87
ggcatagtgc gtgttgtgtt tatgcttaaa                                    30

<210> SEQ ID NO 88
<211> LENGTH: 30
<212> TYPE: DNA
<213> ORGANISM: Saccharomyces cerevisiae

<400> SEQUENCE: 88
aaaatgcaac gcgaggcgag agcgctaatt                                    30

<210> SEQ ID NO 89
<211> LENGTH: 30
<212> TYPE: DNA
<213> ORGANISM: Saccharomyces cerevisiae

<400> SEQUENCE: 89
gaacagttcc acgccacgcc tgatatgagg                                    30

<210> SEQ ID NO 90
<211> LENGTH: 30
<212> TYPE: DNA
<213> ORGANISM: Saccharomyces cerevisiae

<400> SEQUENCE: 90
agcgcgactg cccgacccga agaaggacgc                                    30

<210> SEQ ID NO 91
<211> LENGTH: 30
<212> TYPE: DNA
<213> ORGANISM: Saccharomyces cerevisiae

<400> SEQUENCE: 91
aaaaggttca gtagagtaga aacataaaat                                    30

<210> SEQ ID NO 92
<211> LENGTH: 30
<212> TYPE: DNA
<213> ORGANISM: Saccharomyces cerevisiae

<400> SEQUENCE: 92
ccacaaggac gccttgcctt attcgtatcc                                    30

<210> SEQ ID NO 93
<211> LENGTH: 30
<212> TYPE: DNA
<213> ORGANISM: Saccharomyces cerevisiae

<400> SEQUENCE: 93
cagaatccat gctaggctag aacgcggtga                                    30

<210> SEQ ID NO 94
<211> LENGTH: 30
<212> TYPE: DNA
<213> ORGANISM: Saccharomyces cerevisiae

<400> SEQUENCE: 94
cagctgctac ccaggccagg gattgccacg                                    30

<210> SEQ ID NO 95
```

```
<211> LENGTH: 30
<212> TYPE: DNA
<213> ORGANISM: Saccharomyces cerevisiae

<400> SEQUENCE: 95
ctagccgttc atcaaatcaa tcatgtcaaa                                     30

<210> SEQ ID NO 96
<211> LENGTH: 30
<212> TYPE: DNA
<213> ORGANISM: Saccharomyces cerevisiae

<400> SEQUENCE: 96
caaaaaagtc tagagtagag gaaaaaaacg                                     30

<210> SEQ ID NO 97
<211> LENGTH: 30
<212> TYPE: DNA
<213> ORGANISM: Saccharomyces cerevisiae

<400> SEQUENCE: 97
ttgtcaaagt accgaaccga tcatgacaat                                     30

<210> SEQ ID NO 98
<211> LENGTH: 30
<212> TYPE: DNA
<213> ORGANISM: Saccharomyces cerevisiae

<400> SEQUENCE: 98
gtaacatctt gggcggggcg tttgcaacac                                     30

<210> SEQ ID NO 99
<211> LENGTH: 30
<212> TYPE: DNA
<213> ORGANISM: Saccharomyces cerevisiae

<400> SEQUENCE: 99
actgcctttg ctgagctgag ctggatcaat                                     30

<210> SEQ ID NO 100
<211> LENGTH: 30
<212> TYPE: DNA
<213> ORGANISM: Saccharomyces cerevisiae

<400> SEQUENCE: 100
aatgtaaaag gcaaggcaag aaaacatgta                                     30

<210> SEQ ID NO 101
<211> LENGTH: 30
<212> TYPE: DNA
<213> ORGANISM: Saccharomyces cerevisiae

<400> SEQUENCE: 101
gcctgaattg tagattagat attagataag                                     30

<210> SEQ ID NO 102
<211> LENGTH: 30
<212> TYPE: DNA
<213> ORGANISM: Saccharomyces cerevisiae

<400> SEQUENCE: 102
gtttgacatt gtgaagtgaa gagacataga                                     30

<210> SEQ ID NO 103
```

```
<211> LENGTH: 30
<212> TYPE: DNA
<213> ORGANISM: Saccharomyces cerevisiae

<400> SEQUENCE: 103
tgtcatctac atcatatcat cggtattatt                              30

<210> SEQ ID NO 104
<211> LENGTH: 30
<212> TYPE: DNA
<213> ORGANISM: Saccharomyces cerevisiae

<400> SEQUENCE: 104
cttgttccta gtggcgtggc gctaatggga                              30

<210> SEQ ID NO 105
<211> LENGTH: 30
<212> TYPE: DNA
<213> ORGANISM: Saccharomyces cerevisiae

<400> SEQUENCE: 105
agggccctca gtgatgtgat ggtgttttgt                              30

<210> SEQ ID NO 106
<211> LENGTH: 30
<212> TYPE: DNA
<213> ORGANISM: Saccharomyces cerevisiae

<400> SEQUENCE: 106
ggtattttca ttggtttggt tgtaaaatcg                              30

<210> SEQ ID NO 107
<211> LENGTH: 30
<212> TYPE: DNA
<213> ORGANISM: Saccharomyces cerevisiae

<400> SEQUENCE: 107
caatctaacc accataccat gttggctcac                              30

<210> SEQ ID NO 108
<211> LENGTH: 30
<212> TYPE: DNA
<213> ORGANISM: Saccharomyces cerevisiae

<400> SEQUENCE: 108
cgaaaaatgc accggaccgg ccgcgcatta                              30

<210> SEQ ID NO 109
<211> LENGTH: 30
<212> TYPE: DNA
<213> ORGANISM: Saccharomyces cerevisiae

<400> SEQUENCE: 109
ttacgatctg ctgagctgag attaagcctt                              30

<210> SEQ ID NO 110
<211> LENGTH: 30
<212> TYPE: DNA
<213> ORGANISM: Saccharomyces cerevisiae

<400> SEQUENCE: 110
aaatcgagca atcacgtgat tgctcgattt                              30

<210> SEQ ID NO 111
```

<211> LENGTH: 30
<212> TYPE: DNA
<213> ORGANISM: Saccharomyces cerevisiae

<400> SEQUENCE: 111
ccgacaaacc cccccccccc catttatata					30

<210> SEQ ID NO 112
<211> LENGTH: 30
<212> TYPE: DNA
<213> ORGANISM: Saccharomyces cerevisiae

<400> SEQUENCE: 112
caataagatg tggggtgggg attagtttcg					30

<210> SEQ ID NO 113
<211> LENGTH: 30
<212> TYPE: DNA
<213> ORGANISM: Saccharomyces cerevisiae

<400> SEQUENCE: 113
gtttaacgct tcctgtcctg ggaactgcag					30

<210> SEQ ID NO 114
<211> LENGTH: 30
<212> TYPE: DNA
<213> ORGANISM: Saccharomyces cerevisiae

<400> SEQUENCE: 114
atgaatactc ctcccctccc ttgctgttgg					30

<210> SEQ ID NO 115
<211> LENGTH: 30
<212> TYPE: DNA
<213> ORGANISM: Saccharomyces cerevisiae

<400> SEQUENCE: 115
aatcacaatg gcggcgcggc catcgaccct					30

<210> SEQ ID NO 116
<211> LENGTH: 30
<212> TYPE: DNA
<213> ORGANISM: Saccharomyces cerevisiae

<400> SEQUENCE: 116
gagcaccacg atcgtatcgt tcggtgtact					30

<210> SEQ ID NO 117
<211> LENGTH: 30
<212> TYPE: DNA
<213> ORGANISM: Saccharomyces cerevisiae

<400> SEQUENCE: 117
aaaagcattc tgcagtgcag taattagccg					30

<210> SEQ ID NO 118
<211> LENGTH: 30
<212> TYPE: DNA
<213> ORGANISM: Saccharomyces cerevisiae

<400> SEQUENCE: 118
gtgattctcc atgggatggg tggtttcgct					30

<210> SEQ ID NO 119

```
<211> LENGTH: 30
<212> TYPE: DNA
<213> ORGANISM: Saccharomyces cerevisiae

<400> SEQUENCE: 119
gctggtccag accacaccac aaaaggatgc                                    30

<210> SEQ ID NO 120
<211> LENGTH: 30
<212> TYPE: DNA
<213> ORGANISM: Saccharomyces cerevisiae

<400> SEQUENCE: 120
acttcgactt cgggtcgggt aaaatactct                                    30

<210> SEQ ID NO 121
<211> LENGTH: 30
<212> TYPE: DNA
<213> ORGANISM: Saccharomyces cerevisiae

<400> SEQUENCE: 121
tgacattaat cctaccctac gtgacttaca                                    30

<210> SEQ ID NO 122
<211> LENGTH: 30
<212> TYPE: DNA
<213> ORGANISM: Saccharomyces cerevisiae

<400> SEQUENCE: 122
tttatatccg gtggtgtggt tgcgataagg                                    30

<210> SEQ ID NO 123
<211> LENGTH: 30
<212> TYPE: DNA
<213> ORGANISM: Saccharomyces cerevisiae

<400> SEQUENCE: 123
ctgatgtgcg gtggtgtggg ccttggactt                                    30

<210> SEQ ID NO 124
<211> LENGTH: 30
<212> TYPE: DNA
<213> ORGANISM: Saccharomyces cerevisiae

<400> SEQUENCE: 124
gttgaactac tacggtacgg ttaagggtgc                                    30

<210> SEQ ID NO 125
<211> LENGTH: 30
<212> TYPE: DNA
<213> ORGANISM: Saccharomyces cerevisiae

<400> SEQUENCE: 125
cctatactct accgtaccgt cagggttgat                                    30

<210> SEQ ID NO 126
<211> LENGTH: 30
<212> TYPE: DNA
<213> ORGANISM: Saccharomyces cerevisiae

<400> SEQUENCE: 126
aactagcaaa atggaatgga acaaaaaaaa                                    30

<210> SEQ ID NO 127
```

```
<211> LENGTH: 30
<212> TYPE: DNA
<213> ORGANISM: Saccharomyces cerevisiae

<400> SEQUENCE: 127
ttgactcaac acgggacggg gaaactcacc                                    30

<210> SEQ ID NO 128
<211> LENGTH: 30
<212> TYPE: DNA
<213> ORGANISM: Saccharomyces cerevisiae

<400> SEQUENCE: 128
cattgtgacc ctggcctggc aaatttgcaa                                    30

<210> SEQ ID NO 129
<211> LENGTH: 30
<212> TYPE: DNA
<213> ORGANISM: Saccharomyces cerevisiae

<400> SEQUENCE: 129
atacagctca ctgttctgtt cacgtcgcac                                    30

<210> SEQ ID NO 130
<211> LENGTH: 30
<212> TYPE: DNA
<213> ORGANISM: Saccharomyces cerevisiae

<400> SEQUENCE: 130
tcagattttt cccagcccag tatggctttg                                    30

<210> SEQ ID NO 131
<211> LENGTH: 30
<212> TYPE: DNA
<213> ORGANISM: Saccharomyces cerevisiae

<400> SEQUENCE: 131
tttaacgtgg gcgaagcgaa gaagaaggaa                                    30

<210> SEQ ID NO 132
<211> LENGTH: 30
<212> TYPE: DNA
<213> ORGANISM: Saccharomyces cerevisiae

<400> SEQUENCE: 132
ccattccata tctgttctgt taagtataca                                    30

<210> SEQ ID NO 133
<211> LENGTH: 30
<212> TYPE: DNA
<213> ORGANISM: Saccharomyces cerevisiae

<400> SEQUENCE: 133
ctttgtgcgc tctattctat aatgcagtct                                    30

<210> SEQ ID NO 134
<211> LENGTH: 30
<212> TYPE: DNA
<213> ORGANISM: Saccharomyces cerevisiae

<400> SEQUENCE: 134
aattggtaca gtatggtatg ctcaaaaata                                    30

<210> SEQ ID NO 135
```

```
<211> LENGTH: 30
<212> TYPE: DNA
<213> ORGANISM: Saccharomyces cerevisiae

<400> SEQUENCE: 135
ttgtagcttc cacaacacaa gatgttggct                                  30

<210> SEQ ID NO 136
<211> LENGTH: 30
<212> TYPE: DNA
<213> ORGANISM: Saccharomyces cerevisiae

<400> SEQUENCE: 136
tcttattctc ctgttctgtt gccttcgtac                                  30

<210> SEQ ID NO 137
<211> LENGTH: 30
<212> TYPE: DNA
<213> ORGANISM: Saccharomyces cerevisiae

<400> SEQUENCE: 137
cggttgtata tgcattgcat tgtacgtgcg                                  30

<210> SEQ ID NO 138
<211> LENGTH: 30
<212> TYPE: DNA
<213> ORGANISM: Saccharomyces cerevisiae

<400> SEQUENCE: 138
ttttaataag gcaatgcaat aatattaggt                                  30

<210> SEQ ID NO 139
<211> LENGTH: 30
<212> TYPE: DNA
<213> ORGANISM: Saccharomyces cerevisiae

<400> SEQUENCE: 139
tatcacttac tcgaatcgaa cgttgacatt                                  30

<210> SEQ ID NO 140
<211> LENGTH: 30
<212> TYPE: DNA
<213> ORGANISM: Saccharomyces cerevisiae

<400> SEQUENCE: 140
aaagacatct accgtaccgt gaaggtgccg                                  30

<210> SEQ ID NO 141
<211> LENGTH: 30
<212> TYPE: DNA
<213> ORGANISM: Saccharomyces cerevisiae

<400> SEQUENCE: 141
catattactg cccgccccgc gtaatccaat                                  30

<210> SEQ ID NO 142
<211> LENGTH: 30
<212> TYPE: DNA
<213> ORGANISM: Saccharomyces cerevisiae

<400> SEQUENCE: 142
gtgttagtga atgccatgcc tcaaactctt                                  30

<210> SEQ ID NO 143
```

```
<211> LENGTH: 30
<212> TYPE: DNA
<213> ORGANISM: Saccharomyces cerevisiae

<400> SEQUENCE: 143
aaagagaaaa ataagataag aaaatcttct                                    30

<210> SEQ ID NO 144
<211> LENGTH: 30
<212> TYPE: DNA
<213> ORGANISM: Saccharomyces cerevisiae

<400> SEQUENCE: 144 ccttttttc gtggggtggg aaccgcttta                                     30

<210> SEQ ID NO 145
<211> LENGTH: 30
<212> TYPE: DNA
<213> ORGANISM: Saccharomyces cerevisiae

<400> SEQUENCE: 145 atccacctt gctgcgctgc ttttccttaa                                     30

<210> SEQ ID NO 146
<211> LENGTH: 30
<212> TYPE: DNA
<213> ORGANISM: Saccharomyces cerevisiae

<400> SEQUENCE: 146
tacattcctc ctcatctcat ttgaccgagg                                    30

<210> SEQ ID NO 147
<211> LENGTH: 30
<212> TYPE: DNA
<213> ORGANISM: Saccharomyces cerevisiae

<400> SEQUENCE: 147
gatttatcat gcagtgcagt aatactaata                                    30

<210> SEQ ID NO 148
<211> LENGTH: 30
<212> TYPE: DNA
<213> ORGANISM: Saccharomyces cerevisiae

<400> SEQUENCE: 148
gaattttaag agatcgatca agtcttgtga                                    30

<210> SEQ ID NO 149
<211> LENGTH: 30
<212> TYPE: DNA
<213> ORGANISM: Saccharomyces cerevisiae

<400> SEQUENCE: 149
gttcgatgct gtgcggtgcg ggacttctac                                    30

<210> SEQ ID NO 150
<211> LENGTH: 30
<212> TYPE: DNA
<213> ORGANISM: Saccharomyces cerevisiae

<400> SEQUENCE: 150
cttcacggta acgtaacgta actgaatgtg                                    30

<210> SEQ ID NO 151
```

```
<211> LENGTH: 30
<212> TYPE: DNA
<213> ORGANISM: Saccharomyces cerevisiae

<400> SEQUENCE: 151
caaggagcag agggcagggc acaaaacacc                                       30

<210> SEQ ID NO 152
<211> LENGTH: 30
<212> TYPE: DNA
<213> ORGANISM: Saccharomyces cerevisiae

<400> SEQUENCE: 152
tcaataaaca gccgagccga catacatccc                                       30

<210> SEQ ID NO 153
<211> LENGTH: 30
<212> TYPE: DNA
<213> ORGANISM: Saccharomyces cerevisiae

<400> SEQUENCE: 153
gcgagatgag gtgaagtgaa aagaaactta                                       30

<210> SEQ ID NO 154
<211> LENGTH: 30
<212> TYPE: DNA
<213> ORGANISM: Saccharomyces cerevisiae

<400> SEQUENCE: 154
taaatttcat ccggaccgga agaaaaatga                                       30

<210> SEQ ID NO 155
<211> LENGTH: 30
<212> TYPE: DNA
<213> ORGANISM: Saccharomyces cerevisiae

<400> SEQUENCE: 155
agaaaagtac aattcgatca aggttacggc                                       30

<210> SEQ ID NO 156
<211> LENGTH: 30
<212> TYPE: DNA
<213> ORGANISM: Saccharomyces cerevisiae

<400> SEQUENCE: 156
actgtctttt ccggtccggt cattccaaca                                       30

<210> SEQ ID NO 157
<211> LENGTH: 30
<212> TYPE: DNA
<213> ORGANISM: Saccharomyces cerevisiae

<400> SEQUENCE: 157
atacacgctc atcagatcag acaccacaaa                                       30

<210> SEQ ID NO 158
<211> LENGTH: 30
<212> TYPE: DNA
<213> ORGANISM: Saccharomyces cerevisiae

<400> SEQUENCE: 158
atagtatttc ctagtctagt gatctcggcg                                       30

<210> SEQ ID NO 159
```

```
<211> LENGTH: 30
<212> TYPE: DNA
<213> ORGANISM: Saccharomyces cerevisiae

<400> SEQUENCE: 159
ttcctattct ctagactaga aagtatagga                                    30

<210> SEQ ID NO 160
<211> LENGTH: 32
<212> TYPE: DNA
<213> ORGANISM: Saccharomyces cerevisiae

<400> SEQUENCE: 160
ttataaggtt gtttcgagtt tcatatgtgt tt                                 32

<210> SEQ ID NO 161
<211> LENGTH: 30
<212> TYPE: DNA
<213> ORGANISM: Saccharomyces cerevisiae

<400> SEQUENCE: 161
ttcgagagtg ccattccatt gtaccagact                                    30

<210> SEQ ID NO 162
<211> LENGTH: 30
<212> TYPE: DNA
<213> ORGANISM: Saccharomyces cerevisiae

<400> SEQUENCE: 162
atggatggcg ctcaactcaa gcgtgttacc                                    30

<210> SEQ ID NO 163
<211> LENGTH: 30
<212> TYPE: DNA
<213> ORGANISM: Saccharomyces cerevisiae

<400> SEQUENCE: 163
tccaaatgta ttgtgttgtg agatgaaaat                                    30

<210> SEQ ID NO 164
<211> LENGTH: 30
<212> TYPE: DNA
<213> ORGANISM: Saccharomyces cerevisiae

<400> SEQUENCE: 164
atgattattt cacggcacgg atttcattag                                    30

<210> SEQ ID NO 165
<211> LENGTH: 30
<212> TYPE: DNA
<213> ORGANISM: Saccharomyces cerevisiae

<400> SEQUENCE: 165
atggaaaact agcgcagcgc ataattttgt                                    30

<210> SEQ ID NO 166
<211> LENGTH: 30
<212> TYPE: DNA
<213> ORGANISM: Saccharomyces cerevisiae

<400> SEQUENCE: 166
gagaatcttg tcttgtcttg atgtaacaaa                                    30

<210> SEQ ID NO 167
```

```
<211> LENGTH: 33
<212> TYPE: DNA
<213> ORGANISM: Saccharomyces cerevisiae

<400> SEQUENCE: 167
tagcaaacgt aagtcttcga agtctaaagg ttg                               33

<210> SEQ ID NO 168
<211> LENGTH: 30
<212> TYPE: DNA
<213> ORGANISM: Saccharomyces cerevisiae

<400> SEQUENCE: 168
ttgccgcgaa gctacgctac catccgctgg                                   30

<210> SEQ ID NO 169
<211> LENGTH: 30
<212> TYPE: DNA
<213> ORGANISM: Saccharomyces cerevisiae

<400> SEQUENCE: 169
gtagctcttt tccattccat ggatggacga                                   30

<210> SEQ ID NO 170
<211> LENGTH: 30
<212> TYPE: DNA
<213> ORGANISM: Saccharomyces cerevisiae

<400> SEQUENCE: 170
atgttcattc tctgttctgt agcagtaaga                                   30

<210> SEQ ID NO 171
<211> LENGTH: 30
<212> TYPE: DNA
<213> ORGANISM: Saccharomyces cerevisiae

<400> SEQUENCE: 171
aatcgtaacc ataaaataaa tataagttcc                                   30

<210> SEQ ID NO 172
<211> LENGTH: 30
<212> TYPE: DNA
<213> ORGANISM: Saccharomyces cerevisiae

<400> SEQUENCE: 172
ccttcctgct gtggggtggg cagagagcga                                   30

<210> SEQ ID NO 173
<211> LENGTH: 30
<212> TYPE: DNA
<213> ORGANISM: Saccharomyces cerevisiae

<400> SEQUENCE: 173
tcttagggtt attggattgg tagggttttg                                   30

<210> SEQ ID NO 174
<211> LENGTH: 30
<212> TYPE: DNA
<213> ORGANISM: Saccharomyces cerevisiae

<400> SEQUENCE: 174
agttaacttc cccggcccgg tgttcagtat                                   30

<210> SEQ ID NO 175
```

```
<211> LENGTH: 30
<212> TYPE: DNA
<213> ORGANISM: Saccharomyces cerevisiae

<400> SEQUENCE: 175
atgtgtcatt gaggggaggg aaaatgtaat                                          30

<210> SEQ ID NO 176
<211> LENGTH: 30
<212> TYPE: DNA
<213> ORGANISM: Saccharomyces cerevisiae

<400> SEQUENCE: 176
ggttaacttg ctcgcctcgc catatatatc                                          30

<210> SEQ ID NO 177
<211> LENGTH: 30
<212> TYPE: DNA
<213> ORGANISM: Saccharomyces cerevisiae

<400> SEQUENCE: 177
caaaaaaaga tggagtggag tacagtacgc                                          30

<210> SEQ ID NO 178
<211> LENGTH: 30
<212> TYPE: DNA
<213> ORGANISM: Saccharomyces cerevisiae

<400> SEQUENCE: 178
gatatttacg cttatcttat caatctctgg                                          30

<210> SEQ ID NO 179
<211> LENGTH: 30
<212> TYPE: DNA
<213> ORGANISM: Saccharomyces cerevisiae

<400> SEQUENCE: 179
gccgtggttt ccggaccgga gaaagacgaa                                          30

<210> SEQ ID NO 180
<211> LENGTH: 30
<212> TYPE: DNA
<213> ORGANISM: Saccharomyces cerevisiae

<400> SEQUENCE: 180
tttctggaat tagggtaggg tgacagaatg                                          30

<210> SEQ ID NO 181
<211> LENGTH: 30
<212> TYPE: DNA
<213> ORGANISM: Saccharomyces cerevisiae

<400> SEQUENCE: 181
attactttat ttggcttggc taaagatcct                                          30

<210> SEQ ID NO 182
<211> LENGTH: 30
<212> TYPE: DNA
<213> ORGANISM: Saccharomyces cerevisiae

<400> SEQUENCE: 182
cgttatcata ttgatttgat attgcttatt                                          30

<210> SEQ ID NO 183
```

```
<211> LENGTH: 30
<212> TYPE: DNA
<213> ORGANISM: Saccharomyces cerevisiae

<400> SEQUENCE: 183
ggcaaactat ctcacctcac cagaggtctg                              30

<210> SEQ ID NO 184
<211> LENGTH: 30
<212> TYPE: DNA
<213> ORGANISM: Saccharomyces cerevisiae

<400> SEQUENCE: 184
ctaatagtgc atgatatgat tatatatcaa                              30

<210> SEQ ID NO 185
<211> LENGTH: 30
<212> TYPE: DNA
<213> ORGANISM: Saccharomyces cerevisiae

<400> SEQUENCE: 185
agaaattctc cttggcttgg gattagataa                              30

<210> SEQ ID NO 186
<211> LENGTH: 30
<212> TYPE: DNA
<213> ORGANISM: Saccharomyces cerevisiae

<400> SEQUENCE: 186
tcccgcactg gtgatgtgat acctacaccc                              30

<210> SEQ ID NO 187
<211> LENGTH: 30
<212> TYPE: DNA
<213> ORGANISM: Saccharomyces cerevisiae

<400> SEQUENCE: 187
atcattcatt gccgggccgg aaaaagaaag                              30

<210> SEQ ID NO 188
<211> LENGTH: 30
<212> TYPE: DNA
<213> ORGANISM: Saccharomyces cerevisiae

<400> SEQUENCE: 188
ctcacgctct gcgatgcgat taacagctca                              30

<210> SEQ ID NO 189
<211> LENGTH: 30
<212> TYPE: DNA
<213> ORGANISM: Saccharomyces cerevisiae

<400> SEQUENCE: 189
aggaggaaga accagaccag gcacatgctg                              30

<210> SEQ ID NO 190
<211> LENGTH: 30
<212> TYPE: DNA
<213> ORGANISM: Saccharomyces cerevisiae

<400> SEQUENCE: 190
ttaaatgaac ttcagttcag gaaaataatg                              30

<210> SEQ ID NO 191
```

```
<211> LENGTH: 30
<212> TYPE: DNA
<213> ORGANISM: Saccharomyces cerevisiae

<400> SEQUENCE: 191
ccaatgagtc accagaccag aactgaacaa                                            30
```